United States Patent [19]

Hauser et al.

[11] Patent Number: 5,916,916
[45] Date of Patent: Jun. 29, 1999

[54] 1-ARYLOXY-2-ARYLNAPHTHYL COMPOUNDS, INTERMEDIATES, COMPOSITIONS, AND METHODS

[75] Inventors: Kenneth Lee Hauser, Greencastle; Alan David Palkowitz, Carmel, both of Ind.

[73] Assignee: Eli Lilly and Company, Indianapolis, Ind.

[21] Appl. No.: 08/939,575

[22] Filed: Sep. 29, 1997

Related U.S. Application Data

[60] Provisional application No. 60/027,686, Oct. 10, 1996.

[51] Int. Cl.$^6$ .......................... A01N 37/00; A01N 43/40; A01N 37/10; C07C 69/76
[52] U.S. Cl. .......................... 514/510; 514/319; 514/569; 560/56; 562/466; 546/194
[58] Field of Search ............................ 560/56; 562/466; 546/194; 514/510, 569, 319

[56] References Cited

U.S. PATENT DOCUMENTS

| | | |
|---|---|---|
| 3,274,213 | 9/1966 | Lednicer . |
| 3,293,263 | 12/1966 | Lednicer . |
| 3,313,853 | 4/1967 | Lednicer . |
| 4,133,814 | 1/1979 | Jones et al. . |
| 4,358,593 | 11/1982 | Jones et al. . |
| 4,380,635 | 4/1983 | Peters . |
| 4,418,068 | 11/1983 | Jones . |
| 4,910,212 | 3/1990 | Boyle et al. . |
| 5,470,854 | 11/1995 | von Angerer et al. . |
| 5,484,797 | 1/1996 | Bryant et al. . |
| 5,574,190 | 11/1996 | Palkowitz ................................. 568/440 |

FOREIGN PATENT DOCUMENTS

| | | |
|---|---|---|
| 0062504 | 10/1982 | European Pat. Off. . |
| 0062505 | 10/1982 | European Pat. Off. . |
| 0124369 | 11/1984 | European Pat. Off. . |
| 0703228 | 3/1996 | European Pat. Off. . |
| 0729951 | 9/1996 | European Pat. Off. . |
| 0731093 | 9/1996 | European Pat. Off. . |
| 0733620 | 9/1996 | European Pat. Off. . |
| WO 97/04763 | 2/1997 | WIPO . |

OTHER PUBLICATIONS

Database CAPLUS, No. 125:247626, Palkowitz, 'Preparation of heterocyclyl–substituted 1–phenoxy–2–phenylnaphthalenes as agents for alleviating the symptoms of postmenopausal syndrome' abstract, Sep. 4, 1996.
Durani, N., et al., *Indian J. Chem.*, 22B:489–490 (1983).
Jones, C.D., et al., *J. Med. Chem.*, 35:931–938 (1992).
Lednicer, D., et al., *J. Med. Chem.*, 8:52–57 (1964).
Lednicer, D., et al., *J. Med. Chem.*, 9:172–175 (1965).
Lednicer, D., et al., *J. Med. Chem.*, 10:78–84 (1967).

*Primary Examiner*—Brian M. Burn
*Assistant Examiner*—Brian J. Davis
*Attorney, Agent, or Firm*—Janelle D. Strode

[57] ABSTRACT

The instant invention provides a series of naphthyl compounds having an oxygen linker at the 1-position which are useful as selective estrogen receptor modulators.

14 Claims, No Drawings

1-ARYLOXY-2-ARYLNAPHTHYL COMPOUNDS, INTERMEDIATES, COMPOSITIONS, AND METHODS

CROSS-REFERENCE TO RELATED APPLICATIONS

This application claims priority to provisional application Ser. No. 60/027,686 filed Oct. 10, 1996.

FIELD OF THE INVENTION

This invention relates to organic compounds having biological activity, to pharmaceutical compositions containing the compounds, and to their use in medical methods of treatment. More particularly, the present invention concerns a class of substituted aryloxynaphthalene compounds, pharmaceutical compositions comprising the compounds, chemical process for their synthesis, and the use of the compounds in treating various medical indications associated with inappropriate levels of estrogen and their pathological sequelae.

BACKGROUND OF THE INVENTION

Estrogen is a generic term for estrus-producing steroid compounds. Within the "estrogen group" are the traditional steroids such as 17b-estradiol and estrone (the major estrogens in humans), as well as various metabolites such as the estratriols, sulfates and glucuronides of estradiol and estrone. Also, germane to human medicine, are the steroidal equine estrogens such as the equilins, in that they are administered to humans in preparations, such as Premarin™.

Also, certain compounds known as "anti-estrogens", e.g., tamoxifen, clomiphene, nafoxidene, and raloxifene, demonstrate varying degrees of estrogen agonist properties in some tissues; however they act to antagonize the natural estrogens and their function in other tissues.

Recently, these "anti-estrogens" have been categorized into three different types depending on their degree and mix of estrogen agonist/antagonist properties which is based on their ability to freeze estrogen receptors in different conformational states, cf. D. P. McDonnell, et al., *Molecular Endocrinology*, 9(6): 659–669 (1995). Most germane to the present invention are the so-called "type II anti-estrogens" of which compounds of the current invention belong. The chemical structures of these various anti-estrogen types, although often similar, are poor predictors of pharmacological activity, in that small chemical changes produce varied activity.

Estrogens as biologically active molecules exert their properties by binding to an intracellular receptor. After the receptor and bound ligand are transported to the nucleus of a cell, the complex exerts its effect by binding to certain recognition sites on DNA and allowing certain genes to be expressed. This binding to the receptor and regulation is poorly understood; however, it appears to be crucial to the varying agonist and antagonist properties of the anti-estrogens. Thus, certain types of anti-estrogens allow agonist activity in some tissues, but are antagonists in others. Hence, the term, "selective estrogen receptor modulators" (SERMs) has been proposed to describe these molecules, especially the type II, of which the compounds of the current invention are members.

Estrogen has long been classified as "the female sex hormone" and a great deal of literature describes its activity as such. However, in recent years, research has shown that estrogens have many other homeostatic functions, other than those related to female reproduction and the functioning of sex tissues. Indeed, it has been shown that males possess estrogen receptors and DNA recognition sites and possess the ability to produce estrogens in many tissues, such as those involved in the cardiovascular system. The exact nature of the effects of estrogens in both men and women, outside the productive aspects, are only beginning to be explored and are currently poorly understood.

The majority of the documented activities of the estrogens have been derived from studies in women, since most women suffer from the most obvious effects of estrogen, mainly due to menopause and estrogen dependent cancers. The clinical pathologies associated with estrogen levels and their subsequent function, can be categorized into two main types, i.e., those which are due to a deprivation or lack of estrogen and those which are due to an aberrant physiological response to existing estrogen in estrogen sensitive tissues. SERMS, especially those of the current invention, have the property of being estrogen agonists in those cases where estrogen deprivation is a cause of pathology (mainly in non-sex related tissues) and simultaneously being antagonists of the pathologies caused by abnormal responses to endogenous estrogen (in sex related tissues).

Thus, SERMS of the type II class have the potential to effectively treat a variety of estrogen dependent pathological conditions.

SUMMARY OF THE INVENTION

The present invention provides a class of selective estrogen receptor modulator ("SERM") compounds of the type II class which are useful in the treatment of estrogen-dependent pathological conditions.

In its principal embodiment, the present invention provides a compound of formula 1

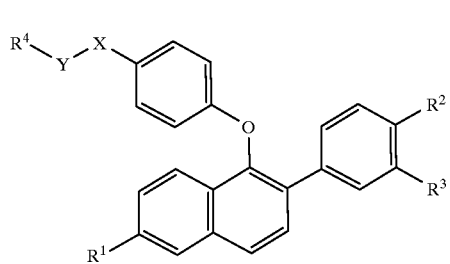

or a pharmaceutically acceptable salt thereof wherein $R^1$ is selected from the group consisting of hydrogen, hydroxy, alkoxy of one to four carbon atoms, alkoxycarbonyl of two to seven carbon atoms, alkoxycarbonyloxy of two to seven carbon atoms, alkylsulfonyloxy, phenoxycarbonyloxy, and aryloxycarbonyl where the aryl portion is unsubstituted phenyl or is phenyl substituted with one or more substituents independently selected from the group consisting of halo, methyl, methoxy, nitro, and trifluoromethyl.

The substituents $R^2$ and $R^3$ are, independently selected from the group consisting of hydrogen, chloro, fluoro, hydroxy, alkoxy of one to four carbon atoms, alkoxycarbonyl of two to seven carbon atoms, alkoxycarbonyloxy of two to seven carbon atoms, alkylsulfonyloxy, phenoxycarbonyloxy, and aryloxycarbonyl where the aryl portion is unsubstituted phenyl or is phenyl substituted with one or more substituents independently selected from the group consisting of halo, methyl, methoxy, nitro, and trifluoromethyl.

The substituent $R^4$ is selected from the group consisting of hydroxy, alkoxy of one to six carbon atoms, cycloalkoxy of four to six carbon atoms, 1-piperidinyl, 1-pyrrolidinyl, methyl-1-pyrrolidinyl, dimethyl-1-pyrrolidino, 4-morpholino, dimethylamino, diethylamino, diisopropylamino, 1-hexamethyleneimino, and aryloxy where wherein the aryl portion is unsubstituted phenyl or is phenyl substituted with one or more substituents independently selected from the group consisting of halo, methyl, methoxy, nitro, and trifluoromethyl.

The linking group X is selected from the group consisting of alkylene of two to four carbon atoms, —CH=CH—, —CH$_2$CH=CH—, and —CH$_2$CH$_2$CH=CH—; and Y is absent or is carbonyl, with the proviso that when Y is absent, R$^4$ may not be hydroxy, —O(C$_1$–C$_6$ alkyl), —O(C$_4$–C$_6$ cycloalkyl), or —OAr.

In another embodiment, the present invention provides a pharmaceutical compositions containing an effective amount of a compound of formula I, either as the sole active component, or together with an effective amount of estrogen or progestin.

In yet another embodiment, the present invention provides a method for the treatment of estrogen-dependent disease states.

DETAILED DESCRIPTION

As used throughout this specification and the appended claims, the the following terms have the ascribed meanings.

"Alkyl" denotes a monovalent group derived by the removal of a single hydrogen atom from a straight or branched hydrocarbon and is typified by methyl, ethyl, propyl, isopropyl, butyl, iso-butyl, sec-butyl, tert-butyl, n-pentyl, iso-pentyl, n-hexyl, and the like.

"Alkylene" means a divalent group derived from methane, ethane or a straight or branched hydrocarbon of three or more carbon atoms by the removal of two hydrogen atoms, and is typified by such groups as methylene (i.e. —CH$_2$—), ethylene, propylene, and the like.

"Alkoxy" or "alkoxyl" means an alkyl group, as defined above, attached to the parent molecular moiety through an oxygen atom and is represented by groups such as methoxy, ethoxy, propoxy, and the like.

"Alkoxycarbonyl" denotes an alkoxy group, as defined above, connected to the parent molecular moiety through a carbonyl group and is typified by such groups as methoxycarbonyl, ethoxycarbonyl, tert-butoxycarbonyl, and the like.

"Alkoxycarbonyloxy" means an alkoxycarbonyl group, as defined above, connected to the parent molecular moiety through an oxygen atom and is represented by such groups as methoxycarbonyloxy, i.e. —OC(O)OCH$_3$, ethoxycarbonyloxy, and the like.

The term "alkylsulfonyloxy" denotes an alkyl group, as defined above, connected to the parent molecular moiety through a sulfonyl (i.e.—SO$_2$—) group, and then through an oxygen atom, and is typified by such groups as methylsulfonyloxy (i.e.—O(SO$_2$)CH$_3$), ethylsulfonyloxy, and the like.

"Aryloxycarbonyl" means an aryl group (within the context of the present invention, unsubstituted phenyl or phenyl substituted as defined above) attached through an oxygen atom and thence through a carbonyl group to the parent molecular moiety.

The term "cycloalkoxy" denotes a monovalent group derived from a cyclic aliphatic hydrocarbon by the removal of one hydrogen atom, attached to the parent molecular moiety through an oxygen atom and is represented by such groups as cyclobutoxy, cyclopentoxy, and the like.

As used herein, the term estrogen includes steroidal compounds having estrogenic activity such as, for example, 17b-estradiol, estrone, conjugated estrogen (Premarin®), equine estrogen 17a-ethynyl estradiol, and the like. As used herein, the term "progestin" includes compounds having progestational activity such as, for example, progesterone, norethylnodrel, nongestrel, megestrol acetate, norethindrone, and the like.

While the genus of compounds defining the present invention has been set forth above, specific examples of compounds contemplated as falling within the scope of the present invention include, but are not limited to, the following.

Examples of compounds of the present invention in which Y is carbonyl and R$^4$ is hydroxy, alkoxy, cycloalkoxy, or aryloxy are:

3-[4-(2-phenyl-6-hydroxynaphth-1-yloxy)phenyl] propenoic acid;

3-[4-(2-phenyl-6-methoxynaphth-1-yloxy)phenyl] propenoic acid;

3-[4-(2-(4-chlorophenyl)naphth-1-yloxy)phenyl] propenoic acid;

3-[4-(2-(3-chloro-4-methoxyphenyl)naphth-1-yloxy) phenyl]propenoic acid;

3-[4-(2-(3-chloro-4-hydroxyphenyl)naphth-1-yloxy) phenyl]propenoic acid;

3-[4-(2-(4-hydroxyphenyl)naphth-1-yloxy)phenyl] propenoic acid;

3-[4-(2-(4-methoxyphenyl)naphth-1-yloxy)phenyl] propenoic acid;

3-[4-(2-(3-chlorophenyl)-6-hydroxynaphth-1-yloxy) phenyl]propenoic acid;

3-[4-(2-(3-chlorophenyl)-6-methoxynaphth-1-yloxy) phenyl]propenoic acid;

3-[4-(2-(4-chlorophenyl)-6-hydroxynaphth-1-yloxy) phenyl]propenoic acid;

3-[4-(2-(4-chlorophenyl)-6-methoxynaphth-1-yloxy) phenyl]propenoic acid;

3-[4-(2-(4-hydroxyphenyl)-6-hydroxynaphth-1-yloxy) phenyl]propenoic acid;

3-[4-(2-(4-methoxyphenyl)-6-hydroxynaphth-1-yloxy) phenyl]propenoic acid;

3-[4-(2-(4-methoxyphenyl)-6-methoxynaphth-1-yloxy) phenyl]propenoic acid;

4-[4-(2-(4-fluorophenyl)-6-hydroxynaphth-1-yloxy) phenyl]but-3-enoic acid;

4-[4-(2-(4-fluorophenyl)-6-methoxynaphth-1-yloxy) phenyl]but-3-enoic acid;

4-[4-(2-(4-hydroxyphenyl)naphth-1-yloxy)phenyl]but-3-enoic acid;

4-[4-(2-(4-methoxyphenyl)naphth-1-yloxy)phenyl]but-3-enoic acid;

4-[4-(2-(3-chloro-4-hydroxyphenyl)naphth-1-yloxy) phenyl]but-3-enoic acid;

4-[4-(2-(3-chloro-4-methoxyphenyl)naphth-1-yloxy) phenyl]but-3-enoic acid;

4-[4-(2-(4-hydroxyphenyl)-6-hydroxynaphth-1-yloxy) phenyl]but-3-enoic acid;

4-[4-(2-(4-methoxyphenyl)-6-hydroxynaphth-1-yloxy) phenyl]but-3-enoic acid;

4-[4-(2-(4-methoxyphenyl)-6-methoxynaphth-1-yloxy) phenyl]but-3-enoic acid;

4-[4-(2-phenyl)naphth-1-yloxy)phenyl]but-3-enoic acid;

3-[4-(2-phenyl-6-hydroxynaphth-1-yloxy)phenyl] propenoic acid;

3-[4-(2-phenyl-6-methoxynaphth-1-yloxy)phenyl] propenoic acid;

3-[4-(2-(3-hydroxyphenyl)-6-hydroxynaphth-1-yloxy) phenyl]propanoic acid;

3-[4-(2-(3-methoxyphenyl)-6-hydroxynaphth-1-yloxy) phenyl]propanoic acid;

3-[4-(2-(3-methoxyphenyl)-6-methoxynaphth-1-yloxy) phenyl]propanoic acid;

3-[4-(2-(4-hydroxyphenyl)-6-hydroxynaphth-1-yloxy) phenyl]propanoic acid;

3-[4-(2-(4-methoxyphenyl)-6-hydroxynaphth-1-yloxy) phenyl]propanoic acid;

3-[4-(2-(4-methoxyphenyl)-6-methoxynaphth-1-yloxy) phenyl]propanoic acid;

3-[4-(2-(4-chlorophenyl)-6-hydroxynaphth-1-yloxy) phenyl]propanoic acid;

3-[4-(2-(4-chlorophenyl)-6-methoxynaphth-1-yloxy) phenyl]propanoic acid;

3-[4-(2-(3-fluorophenyl)-6-hydroxynaphth-1-yloxy) phenyl]propanoic acid;

3-[4-(2-(3-fluorophenyl)-6-methoxynaphth-1-yloxy) phenyl]propanoic acid;

3-[4-(2-phenylnaphth-1-yloxy)phenyl]propanoic acid, ethyl ester;

4-[4-(2-(4-hydroxyphenyl)-6-hydroxynaphth-1-yloxy) phenyl]butanoic acid;

4-[4-(2-(4-methoxyphenyl)-6-hydroxynaphth-1-yloxy) phenyl]butanoic acid;

4-[4-(2-(4-methoxyphenyl)-6-methoxynaphth-1-yloxy) phenyl]butanoic acid;

3-[4-(2-(3-hydroxyphenyl)-6-hydroxynaphth-1-ylyloxy) phenyl]propenoic acid, ethyl ester;

3-[4-(2-(3-methoxyphenyl)-6-methoxynaphth-1-yloxy) phenyl]propenoic acid, ethyl ester;

3-[4-(2-(4-hydroxyphenyl)-6-hydroxynaphth-1-yloxy) phenyl]propenoic acid, ethyl ester;

3-[4-(2-(4-methoxyphenyl)-6-methoxynaphth-1-yloxy) phenyl]propenoic acid, ethyl ester;

3-[4-(2-(3-hydroxyphenyl)-6-hydroxynaphth-1-yloxy) phenyl]propenoic acid, propyl ester;

3-[4-(2-(3-methoxyphenyl)-6-methoxynaphth-1-yloxy) phenyl]propenoic acid, propyl ester;

3-[4-(2-(4-hydroxyphenyl)-6-hydroxynaphth-1-yloxy) phenyl]propenoic acid, butyl ester;

3-[4-(2-(4-methoxyphenyl)-6-methoxynaphth-1-yloxy) phenyl]propenoic acid, butyl ester;

3-[4-(2-(3-hydroxyphenyl)-6-hydroxynaphth-1-yloxy) phenyl]propenoic acid, pentyl ester;

3-[4-(2-(3-methoxyphenyl)-6-methoxynaphth-1-yloxy) phenyl]propenoic acid, pentyl ester;

3-[4-(2-(4-hydroxyphenyl)-6-hydroxynaphth-1-yloxy) phenyl]propenoic acid, hexyl ester;

3-[4-(2-(4-methoxyphenyl)-6-methoxynaphth-1-yloxy) phenyl]propenoic acid, hexyl ester;

3-[4-(2-(3-hydroxyphenyl)naphth-1-yloxy)phenyl] propenoic acid, ethyl ester;

3-[4-(2-(3-methoxyphenyl)naphth-1-yloxy)phenyl] propenoic acid, ethyl ester;

3-[4-(2-(4-hydroxyphenyl)naphth-1-yloxy)phenyl] propenoic acid, ethyl ester;

3-[4-(2-(4-methoxyphenyl)naphth-1-yloxy)phenyl] propenoic acid, ethyl ester;

3-[4-(2-phenylnaphth-1-yloxy)phenyl]propenoic acid, ethyl ester;

3-[4-(2-(4-chlorophenyl)-6-hydroxynaphth-1-yloxy) phenyl]propenoic acid, ethyl ester;

3-[4-(2-(4-chlorophenyl)-6-methoxynaphth-1-yloxy) phenyl]propenoic acid, ethyl ester;

3-[4-(2-(3-fluorophenyl)-6-hydroxynaphth-1-yloxy) phenyl]propenoic acid, ethyl ester;

3-[4-(2-(3-fluorophenyl)-6-methoxynaphth-1-yloxy) phenyl]propenoic acid, ethyl ester;

3-[4-(2-(4-fluorophenyl)-6-hydroxynaphth-1-yloxy) phenyl]propenoic acid, ethyl ester;

3-[4-(2-(4-fluorophenyl)-6-methoxynaphth-1-yloxy) phenyl]propenoic acid, ethyl ester;

3-[4-(2-(3-fluoro-4-methoxyophenyl)-6-methoxynaphth-1-yloxy)phenyl]propenoic acid, ethyl ester;

3-[4-(2-(3-fluoro-4-hydroxyophenyl)-6-hydroxynaphth-1-yloxy)phenyl]propenoic acid, ethyl ester;

4-[4-(2-(3-fluorophenyl)naphth-1-yloxy)phenyl]but-3-enoic acid, ethyl ester;

4-[4-(2-(4-hydroxyphenyl)-6-hydroxynaphth-1-yloxy) phenyl]but-3-enoic acid, ethyl ester;

4-[4-(2-(4-methoxyphenyl)-6-methoxynaphth-1-yloxy) phenyl]but-3-enoic acid, ethyl ester;

4-[4-(2-(4-hydroxyphenyl)-6-hydroxynaphth-1-yloxy) phenyl]but-3-enoic acid, pentyl ester;

4-[4-(2-(4-methoxyphenyl)-6-methoxynaphth-1-yloxy) phenyl]but-3-enoic acid, pentyl ester;

4-[4-(2-(4-hydroxyphenyl)-6-hydroxynaphth-1-yloxy) phenyl]but-3-enoic acid, cyclohexyl ester;

4-[4-(2-(4-methoxyphenyl)-6-methoxynaphth-1-yloxy) phenyl]but-3-enoic acid, cyclohexyl ester;

4-[4-(2-(4-hydroxyphenyl)naphth-1-yloxy)phenyl]but-3-enoic acid, cyclohexyl ester;

4-[4-(2-(4-methoxyphenyl)naphth-1-yloxy)phenyl]but-3-enoic acid, cyclohexyl ester;

4-[4-(2-(4-hydroxyphenyl)-6-hydroxynaphth-1-yloxy) phenyl]but-3-enoic acid, phenyl ester;

4-[4-(2-(4-methoxyphenyl)-6-methoxynaphth-1-yloxy) phenyl]but-3-enoic acid, phenyl ester;

4-[4-(2-(4-hydroxyphenyl)-6-hydroxynaphth-1-yloxy) phenyl]but-3-enoic acid, 4-methylphenyl ester;

4-[4-(2-(4-methoxyphenyl)-6-methoxynaphth-1-yloxy) phenyl]but-3-enoic acid, 4-methylphenyl ester;

3-[4-(2-(3-hydroxyphenyl)naphth-1-yloxy)phenyl] propanoic acid, ethyl ester;

3-[4-(2-(3-methoxyphenyl)naphth-1-yloxy)phenyl] propanoic acid, ethyl ester;

3-[4-(2-(4-hydroxyphenyl)naphth-1-yloxy)phenyl] propanoic acid, ethyl ester;

3-[4-(2-(4-methoxyphenyl)naphth-1-yloxy)phenyl] propanoic acid, ethyl ester;

3-[4-(2-(3-hydroxyphenyl)-6-hydroxynaphth-1-yloxy) phenyl]propanoic acid, ethyl ester;

3-[4-(2-(3-methoxyphenyl)-6-methoxynaphth-1-yloxy) phenyl]propanoic acid, ethyl ester;

3-[4-(2-(3-hydroxyphenyl)-6-hydrxynaphth-1-yloxy) phenyl]propanoic acid, propyl ester;

3-[4-(2-(3-methoxyphenyl)-6-methoxynaphth-1-yloxy) phenyl]propanoic acid, propyl ester;

3-[4-(2-(3-hydroxyphenyl)-6-hydroxynaphth-1-yloxy) phenyl]propanoic acid, pentyl ester;

3-[4-(2-(3-methoxyphenyl)-6-methoxynaphth-1-yloxy) phenyl]propanoic acid, pentyl ester;
3-[4-(2-(3-fluorophenyl)-6-hydroxynaphth-1-yloxy) phenyl]propanoic acid, ethyl ester;
3-[4-(2-(3-fluorophenyl)-6-methoxynaphth-1-yloxy) phenyl]propanoic acid, ethyl ester;
3-[4-(2-(4-fluorophenyl)-6-hydroxynaphth-1-yloxy) phenyl]propanoic acid, ethyl ester;
3-[4-(2-(4-fluorophenyl)-6-methoxynaphth-1-yloxy) phenyl]propanoic acid, ethyl ester;
3-[4-(2-(3-fluoro-4-hydroxyphenyl)-6-hydroxynaphth-1-yloxy)phenyl]propanoic acid, ethyl ester;
3-[4-(2-(3-fluoro-4-methoxyphenyl)-6-methoxynaphth-1-yloxy)phenyl]propanoic acid, ethyl ester;
3-[4-(2-(4-chlorophenyl)-6-hydroxynaphth-1-yloxy) phenyl]propanoic acid, ethyl ester;
3-[4-(2-(4-chlorophenyl)-6-methoxynaphth-1-yloxy) phenyl]propanoic acid, ethyl ester;
3-[4-(2-(4-hydroxyphenyl)-6-hydroxynaphth-1-yloxy) phenyl]propanoic acid, ethyl ester;
3-[4-(2-(4-methoxyphenyl)-6-methoxynaphth-1-yloxy) phenyl]propanoic acid, ethyl ester;
3-[4-(2-(4-fluorophenyl)naphth-1-yloxy)phenyl] propanoic acid, butyl ester;
3-[4-(2-(4-methoxyphenyl)naphth-1-yloxy)phenyl] propanoic acid, butyl ester;
3-[4-(2-(4-hydroxyphenyl)naphth-1-yloxy)phenyl] propanoic acid, butyl ester;
3-[4-(2-(4-hydroxyphenyl)-6-hydroxynaphth-1-yloxy) phenyl]propanoic acid, hexyl ester;
3-[4-(2-(4-methoxyphenyl)-6-methoxynaphth-1-yloxy) phenyl]propanoic acid, hexyl ester;
4-[4-(2-(3-hydroxyphenyl)-6-hydroxynaphth-1-yloxy) phenyl]butanoic acid, ethyl ester;
4-[4-(2-(4-hydroxyphenyl)-6-hydroxynaphth-1-yloxy) phenyl]butanoic acid, ethyl ester;
4-[4-(2-(4-methoxyphenyl)-6-hydroxynaphth-1-yloxy) phenyl]butanoic acid, ethyl ester;
4-[4-(2-(4-methoxyphenyl)-6-methoxynaphth-1-yloxy) phenyl]butanoic acid, ethyl ester;
4-[4-(2-(4-hydroxyphenyl)-6-hydroxynaphth-1-yloxy) phenyl]butanoic acid, ethyl ester;
4-[4-(2-(4-methoxyphenyl)-6-methoxynaphth-1-yloxy) phenyl]butanoic acid, ethyl ester;
4-[4-(2-(4-hydroxyphenyl)-6-hydroxynaphth-1-yloxy) phenyl]butanoic acid, pentyl ester;
4-[4-(2-(4-methoxyphenyl)-6-methoxynaphth-1-yloxy) phenyl]butanoic acid, pentyl ester;
4-[4-(2-(4-hydroxyphenyl)-6-hydroxynaphth-1-yloxy) phenyl]butanoic acid, cyclohexyl ester;
4-[4-(2-(4-methoxyphenyl)-6-methoxynaphth-1-yloxy) phenyl]butanoic acid, cyclohexyl ester;
4-[4-(2-(4-hydroxyphenyl)-6-hydroxynaphth-1-yloxy) phenyl]butanoic acid, phenyl ester;
4-[4-(2-(4-methoxyphenyl)-6-methoxynaphth-1-yloxy) phenyl]butanoic acid, phenyl ester;
4-[4-(2-(4-hydroxyphenyl)-6-hydroxynaphth-1-yloxy) phenyl]butanoic acid, 4-methylphenyl ester; and
4-[4-(2-(4-methoxyphenyl)-6-methoxynaphth-1-yloxy) phenyl]butanoic acid, 4-methylphenyl ester.

Examples of compounds of the present invention in which Y is carbonyl, and $R^4$ is 1-piperidinyl, 1-pyrrolidinyl, methyl-1-pyrrolidinyl, dimethyl-1-pyrrolidino, 4-morpholino, dimethylamino, diethylamino, diisopropylamino, or 1-hexamethyleneimino, are:

3-[4-(2-(4-hydroxyphenyl)naphth-1-yloxy)phenyl] propenoic acid, N,N-diethylamide;
3-[4-(2-(4-methoxyphenyl)naphth-1-yloxy)phenyl] propenoic acid, N,N-diethylamide;
3-[4-(2-(4-hydroxyphenyl)-6-hydroxynaphth-1-yloxy) phenyl]propenoic acid, N,N-dimethylamide;
3-[4-(2-(4-methoxyphenyl)-6-methoxynaphth-1-yloxy) phenyl]propenoic acid, N,N-dimethylamide;
3-[4-(2-(4-hydroxyphenyl)-6-hydroxynaphth-1-yloxy) phenyl]propenoic acid, 1-pyrrolidinylamide;
3-[4-(2-(4-methoxyphenyl)-6-methoxynaphth-1-yloxy) phenyl]propenoic acid, 1-pyrrolidinylamide;
3-[4-(2-phenyl-6-hydroxynaphth-1-yloxy)phenyl] propenoic acid, 1-piperidinylamide;
3-[4-(2-phenyl-6-methoxynaphth-1-yloxy)phenyl] propenoic acid, 1-piperidinylamide;
3-[4-(2-(4-hydroxyphenyl)naphth-1-yloxy)phenyl] propenoic acid, 1-piperidinylamide;
3-[4-(2-(4-methoxyphenyl)naphth-1-yloxy)phenyl] propenoic acid, 1-piperidinylamide;
3-[4-(2-(3-hydroxyphenyl)-6-hydroxynaphth-1-yloxy) phenyl]propenoic acid, 1-piperidinylamide;
3-[4-(2-(3-methoxyphenyl)-6-methoxynaphth-1-yloxy) phenyl]propenoic acid, 1-piperidinylamide;
3-[4-(2-(4-hydroxyphenyl)-6-hydroxynaphth-1-yloxy) phenyl]propenoic acid, 1-piperidinylamide;
3-[4-(2-(4-methoxyphenyl)-6-methoxynaphth-1-yloxy) phenyl]propenoic acid, 1-piperidinylamide;
4-[4-(2-(3-hydroxyphenyl)-6-hydroxynaphth-1-yloxy) phenyl]but-3-enoic acid, 1-piperidinylamide;
4-[4-(2-(3-methoxyphenyl)-6-methoxynaphth-1-yloxy) phenyl]but-3-enoic acid, 1-piperidinylamide;
4-[4-(2-(4-hydroxyphenyl)-6-hydroxynaphth-1-yloxy) phenyl]but-3-enoic acid, 1-piperidinylamide;
4-[4-(2-(4-methoxyphenyl)-6-methoxynaphth-1-yloxy) phenyl]but-3-enoic acid, 1-piperidinylamide;
4-[4-(2-(4-hydroxyphenyl)naphth-1-yloxy)phenyl]but-3-enoic acid, 1-piperidinylamide;
4-[4-(2-(4-methoxyphenyl)naphth-1-yloxy)phenyl]but-3-enoic acid, 1-piperidinylamide;
4-[4-(2-phenyl-6-hydroxynaphth-1-yloxy)phenyl]but-3-enoic acid, 1-piperidinylamide;
4-[4-(2-phenyl-6-methoxynaphth-1-yloxy)phenyl]but-3-enoic acid, 1-piperidinylamide;
3-[4-(2-(4-hydroxyphenyl)naphth-1-yloxy)phenyl] propanoic acid, N,N-diethylamide;
3-[4-(2-(4-methoxyphenyl)naphth-1-yloxy)phenyl] propanoic acid, N,N-diethylamide;
3-[4-(2-(3-hydroxyphenyl)-6-methoxynaphth-1-yloxy) phenyl]propanoic acid, 1-piperidinylamide;
3-[4-(2-(3-methoxyphenyl)-6-methoxynaphth-1-yloxy) phenyl]propanoic acid, 1-piperidinylamide;
3-[4-(2-(4-hydroxyphenyl)-6-methoxynaphth-1-yloxy) phenyl]propanoic acid, 1-piperidinylamide; and
3-[4-(2-(4-methoxyphenyl)-6-methoxynaphth-1-yloxy) phenyl]propanoic acid, 1-piperidinylamide.

Compounds of the present invention in which Y is absent and $R^4$ is 1-piperidinyl, 1-pyrrolidinyl, methyl-1-pyrrolidinyl, dimethyl-1-pyrrolidino, 4-morpholino, dimethylamino, diethylamino, diisopropylamino, or 1-hexamethyleneimino, are:

1-[4-[3-(piperidin-1-yl)propyl]phenoxy]-2-(4-methoxyphenyl)-6-methoxynaphthalene;
1-[4-[3-(1-piperidinyl)propyl]phenoxy]-2-(3-methoxyphenyl)-6-methoxynaphthalene;
1-[4-[3-(1-piperidinyl)propyl]phenoxy]-2-(3,4-dimethoxyphenyl)-6-methoxynaphthalene;
1-[4-[3-(1-piperidinyl)propyl]phenoxy]-2-(3-fluorophenyl)-6-methoxynaphthalene;
1-[4-[3-(1-piperidinyl)propyl]phenoxy]-2-(4-chlorophenyl)-6-methoxynaphthalene;
1-[4-[3-(1-piperidinyl)propyl]phenoxy]-2-(4-methoxyphenyl)naphthalene;
1-[4-[3-(1-pyrolidinyl)propyl]phenoxy]-2-(4-methoxyphenyl)-6-methoxynaphthalene;
1-[4-[3-(N,N-dimethyl)propyl]phenoxy]-2-(4-methoxyphenyl)-6-methoxynaphthalene;
1-[4-[3-(1-hexamethyleneimino)propyl]phenoxy]-2-(4-methoxyphenyl)-6-methoxynaphthalene;
1-[4-[3-(N,N-dimethyl)propyl]phenoxy]-2-(4-methoxyphenyl)-6-methoxynaphthalene;
1-[4-[3-(1-pyrolidinyl)propyl]phenoxy]-2-(3-methoxyphenyl)-6-methoxynaphthalene;
1-[4-[3-(1-piperidinyl)prop-2-enyl]phenoxy]-2-(4-methoxyphenyl)-6-methoxynaphthalene;
1-[4-[3-(1-piperidinyl)prop-2-enyl]phenoxy]-2-(3-methoxyphenyl)-6-methoxynaphthalene;
1-[4-[3-(1-piperidinyl)prop-2-enyl]phenoxy]-2-(4-methoxyphenyl)naphthalene;
1-[4-[3-(1-piperidinyl)prop-2-enyl]phenoxy]-2-phenyl-6-methoxynaphthalene;
1-[4-[3-(1-hexamethyleneimino)prop-2-enyl]phenoxy]-2-(4-methoxyphenyl)-6-methoxynaphthalene;
1-[4-[3-(1-piperidinyl)prop-2-enyl]phenoxy]-2-(4-chloro-phenyl)-6-methoxynaphthalene;
1-[4-[3-(N,N-dimethyl)prop-2-enyl]phenoxy]-2-(4-methoxy-phenyl)-6-methoxynaphthalene;
1-[4-[4-(1-piperidinyl)but-3-enyl]phenoxy]-2-(4-methoxy-phenyl)-6-methoxynaphthalene;
1-[4-[4-(1-piperidinyl)but-3-enyl]phenoxy]-2-(3-methoxy-phenyl)-6-methoxynaphthalene;
1-[4-[4-(1-pyrolidinyl)but-3-enyl]phenoxy]-2-(4-methoxy-phenyl)-6-methoxynaphthalene;
1-[4-[4-(1-piperidinyl)but-3-enyl]phenoxy]-2-(4-methoxyphenyl)naphthalene;
1-[4-[4-(1-piperidinyl)but-3-enyl]phenoxy]-2-phenyl-6-methoxynaphthalene;
1-[4-[4-(1-piperidinyl)but-3-enyl]phenoxy]-2-(3-fluorophenyl)-6-methoxynaphthalene;
1-[4-[4-(1-piperidinyl)butyl]phenoxy]-2-(4-methoxyphenyl)-6-methoxynaphthalene;
1-[4-[4-(1-piperidinyl)butyl]phenoxy]-2-(3-methoxyphenyl)-6-methoxynaphthalene;
1-[4-[4-(1-piperidinyl)butyl]phenoxy]-2-(4-methoxyphenyl)naphthalene;
1-[4-[4-(1-piperidinyl)butyl]phenoxy]-2-phenyl-6-methoxynaphthalene;
1-[4-[4-(1-pyrolidinyl)butyl]phenoxy]-2-(4-methoxyphenyl)-6-methoxynaphthalene; and
1-[4-[4-(1-piperidinyl)butyl]phenoxy]-2-(4-fluorophenyl)-6-methoxynaphthalene.

Preferred compounds of the present invention are compounds of Formula I above in which $R^1$, $R^2$ and $R^3$ are selected from halogen, hydroxy, and alkoxy, most preferably methoxy.

Particularly preferred compounds of the present invention are compounds in which Y is absent and $R^4$ is selected from 1-piperidinyl, 1-pyrrolidinyl, methyl-1-pyrrolidinyl, dimethyl-1-pyrrolidino, 4-morpholino, dimethylamino, diethylamino, diisopropylamino, or 1-hexamethyleneimino, most preferably 1-pyrrolidinyl and 1-piperidinyl.

By virtue of their ability to act as so-called type II selective estrogen receptor modulators ("SERMs"), the compounds of the present invention are useful for the treatment of disease states associated with the deprivation or lack of estrogen as well as pathological conditions which are due to an aberrant physiological response to existing estrogen in estrogen sensitive tissues. SERMs, especially is those of the current invention, have the property of being estrogen agonists in those cases where estrogen deprivation is a cause of pathology (mainly in non-sex related tissues) and simultaneously being antagonists of the pathologies caused by abnormal responses to endogenous estrogen (in sex related tissues).

Thus, compounds of the present invention are useful in the treatment of pathological conditions associated with estrogen deprivation such as bone loss or bone resorption, due to either menopause or ovariectomy.

Moreover, the compounds of the present invention are useful in the treatment of pathologies caused by abnormal responses to enogenous estrogen (in sex related tissues), including their usefulness in lower serum cholesterol levels.

A post-menopausal model was used in which the effects of different treatments upon circulating lipids and upon osteoporosis were determined. This model demonstrates the ulitity of the compounds of the current invention to treat pathologies caused by the deprivation of estrogen.

Seventy-five day old female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.20°±1.70° C. with a minimum relative humidity of 40%. The photoperiod in the room is 12 hours light and 12 hours dark.

Dosing Regimen Tissue Collection

After a one week acclimation period (therefore, two weeks post-OVX) daily dosing with test compound is initiated. 17a-ethynyl estradiol or the test compound are given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine: Xylazine (2:1, V:V) mixture and a blood sample is collected by cardiac puncture. The animals are then sacrificed by asphyxiation with $CO_2$, the uterus is removed through a midline incision, and a wet uterine weight is determined.

Cholesterol Analysis

Blood samples are allowed to clot at ambient temperature for 2 hours, and serum is obtained following centrifugation for 10 minutes at 3000 rpm. Serum cholesterol is determined using a Boehringer Mannheim Diagnostics high performance cholesterol assay. Briefly, the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Uterine Eosinophil Peroxidase (EPO) Assay

Uteri are kept at 4° C. until time of enzymatic analysis. The uteri are then homogenized in 50 volumes of 50 mM Tris buffer (pH −8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosonophils in the uterus is an indication of estrogenic activity of a compound. The maximal velocity of a 15 second interval is determined over the initial, linear portion of the reaction curve.

Source of Compound 17a-ethynyl estradiol was obtained from Sigma Chemical Co., St. Louis, Mo.

Selected compounds of formula I were evaluated in the above assay. These results are presented in Table 1.

TABLE 1

| Compound | Dose (mg/kg)[a] | Uterine Weight (% Inc.)[b] | Uterine Eosinophil ($V_{max}$)[c] | Serum Cholesterol (% Dec.)[d] |
|---|---|---|---|---|
| EE2[e] | 0.1 | 96.0* | 54.6* | 75.9* |
| Example 3 | 0.1 | 2.2 | 3.0 | 12.4 |
|  | 1.0 | −3.7 | 0.6 | 34.7* |
|  | 10.0 | 9.7 | 3.0 | 37.6* |
| Example 7 | 0.1 | 57.3* | 7.2 | — |
|  | 1.0 | 79.7* | 106.2* | 52.3* |
|  | 10.0 | 111.4* | 132.9* | 51/6* |

[a]mg/kg PO
[b]Uterine Weight % increase versus the ovarierectomized controls
[c]Eosinphil peroxidase Vmaxium
[d]Serum cholesterol decrease versus ovariectomized controls
[e]17-a-Ethynyl-estradiol
*p < .05

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the present invention and ethynyl estradiol ($EE_2$) in 20% hydroxypropyl b-cyclodextrin are orally administered to test animals.

As evidence of the utility of the compounds of the current invention to treat pathologies derived from the inappropriate presence of estrogen, the following models are described, below.

MCF-7 Proliferation Assay

MCF-7 breast adenocarcinoma cells (ATCC HTB 22) are maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 ug/mL) (maintenance medium). Ten days prior to assay, MCF-7 cells are switched to maintenance medium supplemented with 10% dextran coated charcoal stripped fetal bovine serum (DCC-FBS) assay medium) in place of 10% FBS to deplete internal stores of steroids. MCF-7 cells are removed from maintenance flasks using cell dissociation medium (Ca++/Mg++ free HBSS (phenol red-free) supplemented with 10 mM HEPES and 2 mM EDTA). Cells are washed twice with assay medium and adjusted to 80,000 cells/mL. Approximately 100 mL (8,000 cells) are added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control are prepared in assay medium and 50 mL transferred to triplicate microcultures followed by 50 mL assay medium for a final volume of 200 mL. After an additional 48 hours at 37° C. in a 5% $CO_2$ humidified incubator, microcultures are pulsed with tritiated thymidine (1 uCi/well) for 4 hours. Cultures are terminated by freezing at −70° C. for 24 hours followed by thawing and harvesting of microcultures using a Skatron Semiautomatic Cell Harvester. Samples are counted by liquid scintillation using a Wallac BetaPlace b counter. Activity of a compound of formula I in the present assay demonstrates that the compound is of potential for treating hormonally-dependent cancer, particularly breast cancer. For example, the compound of Example 3 inhibits cell growth in this assay with an $IC_{50}$ 400 nM. The compound of Example 7 is extremely potent in this assay with an $IC_{50}$ of 100 pM.

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

The present invention also provides a method of alleviating estrogen deprivation in women which comprises the aforementioned method using compounds of Formula I and further comprises administering to a woman an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, infra, indicates that the combination treatments are useful for alleviating the symptoms of post-menopausal symptoms in women.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin, and norethylnodrel and norethindrone are preferred progestin-based agents.

The method of administration of each estrogen- and progestin-based agent is consistent with that which is known in the art. For the majority of the methods of the present invention, compounds of Formula I are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "effective amount" means an amount of compound (formula I) of the present invention which is capable of alleviating, inhibiting, preventing, ameliorating, reversing, obviating, or lessening the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 80 mg/day.

The compounds of this invention can be administered by a variety of routes including oral, rectal, transdermal, subucutaneus, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt or solvate thereof, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, solvent, excipients and salt must be compatible with the other ingredients of the formulation, and not deleterious to the recipient thereof.

Pharmaceutical formulations of the present invention can be prepared by procedures known in the art using well known and readily available ingredients. For example, the compounds of formula I, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula 1, alone or in combination with a pharmaceutical agent of the present invention, generally will be administered in a convenient formulation. The following formulation examples only are illustrative and are not intended to limit the scope of the present invention.

Formulations

In the formulations which follow, "active ingredient" means a compound of Formula 1, or a salt or solvate thereof.

Formulation 1: Gelatin Capsules

Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 2: Tablets

| Ingredient | Quantity (mg/tablet) |
|---|---|
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 3: Tablets

| Ingredient | Quantity (mg/tablet) |
| --- | --- |
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 4: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:
Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:
Formulation 7: Intravenous Solution

| Ingredient | Quantity |
| --- | --- |
| Active ingredient | 50 mg |
| Isotonic saline | 1,000 mL |

The solution of the above ingredients is intravenously administered to a patient at a rate of about 1 mL per minute.

Formulation 8: Combination Capsule I

| Ingredient | Quantity (mg/capsule) |
| --- | --- |
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 9: Combination Capsule II

| Ingredient | Quantity (mg/capsule) |
| --- | --- |
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

Formulation 10: Combination Tablet

| Ingredient | Quantity (mg/capsule) |
| --- | --- |
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

Synthesis of Compounds of the Invention

Compounds of the present invention are prepared, starting with the steps depicted in Reaction Scheme I in which $R^{1a}$ is —H or —$OR^5$, where $R^5$ is a hydroxy protecting group, and $R^{2a}$ and $R^{3a}$ are —H, halo, or —$OR^5$.

Suitable hydroxyl protecting groups are those discussed in T. W. Greene, et al., "Protective Groups in Organic Synthesis," 2nd Edition, John Wiley & Sons, Inc., New York, 1991.

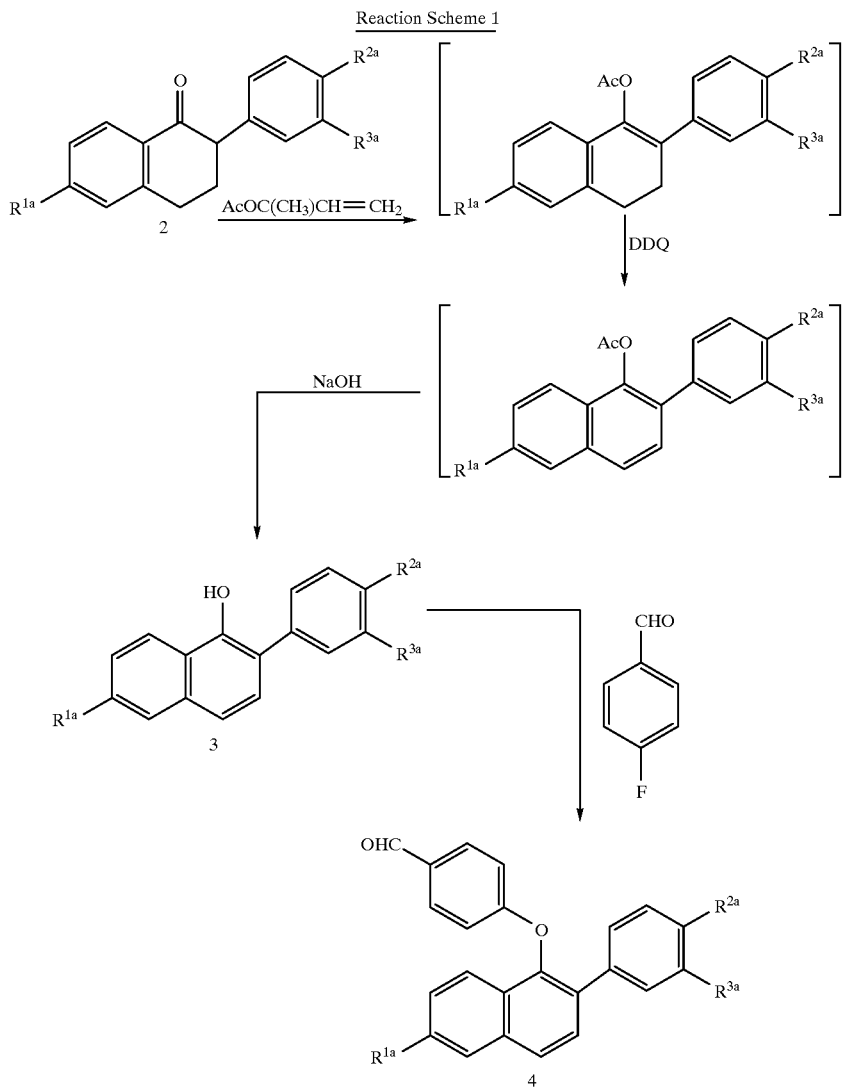

Reaction Scheme 1

The starting tetralone compounds, 2, are well known in the art and are prepared essentially as described by Boyle, et al., in U.S. Pat. No. 4,910,212 which is incorporated herein by reference. See., also, Collins, D. J., et al., *Aust. J. Chem.*, 41:745–756 (1988); and Collins, D. J., et al., *Aust. J. Chem.*, 37:2279–2294 (1984).

As shown in Reaction Scheme 1, a ketone of formula 2 is aromatized, providing a phenol of formula 3, which is then reacted with a 4-halobenzaldehyde to give a biaryl ether of formula 4.

In the first step, the ketone, 2, is converted to a phenol of formula 3 via a three-step protocol, essentially as described by Wang, G., et al., *M. Syn. Commun.*, 21:989 (1991). A ketone of formula 2 is enolized by heating it under reflux in an appropriate enolic ester solvent, in the presence of an acid catalyst. The resulting enolacetate is directly oxidized to a naphtholacetate which is then hydrolyzed to a phenol of formula 3.

In converting a ketone of formula 2 to its corresponding enol, various known acid catalysts can be used. Preferably, non-aqueous acids, particularly p-toluenesulfonic acid is preferred. A preferred enolic ester solvent is isopropenylacetate.

The reaction takes from about 6 to about 48 hours to complete. The enol product from this reaction is not isolated, but upon completion of the reaction, the resulting solution is treated with an appropriate oxidant and heated under reflux for about 1 to about 3 hours.

Appropriate oxidants for this reaction step are limited to those known in the art which can lead to the elimination of a hydrogen atom from a saturated system to give an aromatized system. Such oxidants include, for example, hydrogenation catalysts such as platinum, palladium, and nickel, elemental sulfur and selenium, and quinones. For the present application, quinone oxidants, especially 2,3-dichloro-5,6-dicyano-1,4-benzoquinone (DDQ) are preferred. About 1 to 2 equivalents of DDQ per equivalent of substrate will drive the present process phase.

The resulting product is the naphtholacetate, which is then subjected to hydrolysis to provide a compound of formula 3.

The hydrolysis step is accomplished via either acid or basic hydrolysis of the substrate in a polar protic solvent such as water or one or more solvents containing an alcohol such as methanol or ethanol. A cosolvent such as tetrahydrofuran (THF) or dioxane also may be added to the solution to aid solubility. Appropriate bases for this phase include sodium hydroxide, potassium hydroxide, lithium hydroxide, and the like. Appropriate acids include, for example, hydrochloric acid, methanesulfonic acid, p-toluenesulfonic acid, and the like.

This final hydrolysis step, shown in Scheme 1, can be run at ambient temperature and is complete typically from 1 to about 12 hours. Completion of the hydrolysis step is followed by means of standard chromatographic techniques such as thin layer chromatography.

In the next step of Scheme 1, the phenol of formula 3 is first reacted with a base, followed by the addition of a 4-halobenzaldehyde in a polar aprotic solvent, under an inert atmosphere such as nitrogen, to give a biarylether of formula 4. This reaction is well known in the art and is carried out essentially as described by Yeager, G. W., et al., *Synthesis*, 63 (1991).

More particularly, 1 equivalent of a formula 3 compound is first treated with at least 1 equivalent of an alkali metal hydride, preferably sodium hydride, or carbonate in an appropriate solvent, followed by a dropwise addition of a 4-halobenzaldehyde, preferably 4-fluorobenzaldehyde, in the same solvent as used with the substrate.

Appropriate solvents for this reaction are those solvents or mixture of solvents which remain inert throughout the reaction. N,N-dimethylformamide (DMF), especially the anhydrous form thereof, is preferred. A preferred temperature range for this reaction is from about 30° C. to about 100° C. Under the preferred reaction conditions, a formula IV compound is prepared in about 24 to about 48 hours.

Typical examples of compounds of formula 4 prepared by the process of Reaction Scheme 1 include:

1-(4-formylphenoxy)-2-(4-methoxyphenyl)-6-methoxynaphthalene;
1-(4-formylphenoxy)-2-(4-methoxyphenyl)naphthalene;
1-(4-formylphenoxy)-2-(3-methoxyphenyl)-6-methoxynaphthalene;
1-(4-formylphenoxy)-2-(3,4-di-methoxyphenyl)-6-methoxynaphthalene;
1-(4-formylphenoxy)-2-(3-methoxyphenyl)naphthalene;
1-(4-formylphenoxy)-2-(4-chlorophenyl)-6-methoxynaphthalene;
1-(4-formylphenoxy)-2-(4-fluorophenyl)-6-methoxynaphthalene;
1-(4-fornylphenoxy)-2-(4-chlorophenyl)naphthalene;
1-(4-formylphenoxy)-2-(4-fluorophenyl)naphthalene;
1-(4-formylphenoxy)-2-(3-fluorophenyl)-6-methoxynaphthalene;
1-(4-formylphenoxy)-2-(3-chlorophenyl)-6-methoxynaphthalene;
1-(4-formylphenoxy)-2-phenylnaphthalene;
1-(4-formylphenoxy)-2-(3-chlorophenyl)naphthalene;
1-(4-formylphenoxy)-2-(3-fluorophenyl)naphthalene;
1-(4-formylphenoxy)-2-(3-fluoro-4-methoxyphenyl)-6-methoxy-naphthalene; and
1-(4-formylphenoxy)-2-(3-chloro-4-methoxyphenyl)-6-methoxynaphthalene.

The synthesis of the compounds of the present invention continues as depicted in Reaction Scheme 2 in which $R^{1a}$, $R^{2a}$, and $R^{3a}$ have the meanings ascribed above, $X^a$ is —CH=CH— or —CH$_2$CH=CH—, $Y^a$ is —CO—; and $R^{4a}$ is —O(C$_1$–C$_6$) alkyl, —O(C$_4$–C$_6$) cycloalkyl, or —OAr, where Ar is phenyl or substituted phenyl.

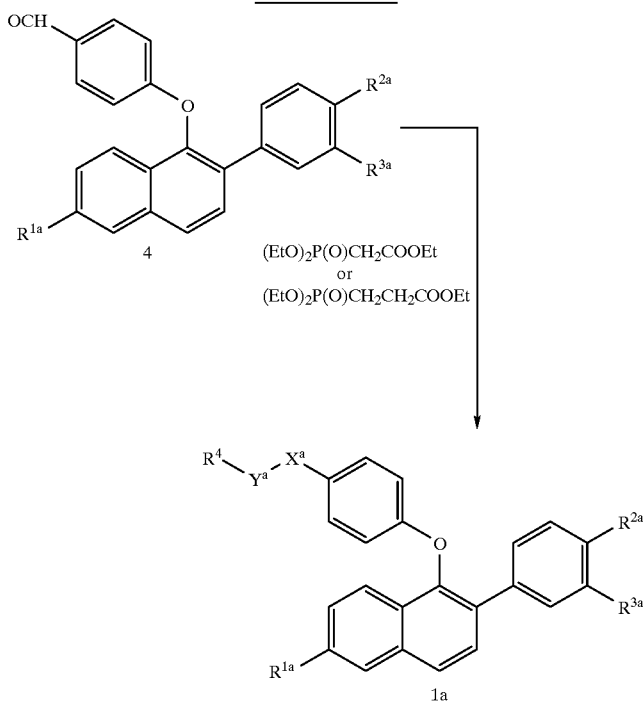

Reaction Scheme 2

As shown in Reaction Scheme 2, an alkyl ester is added to the aldehyde compound of formula 4 to form an alkene of formula 1a. This general type of reaction may be accomplished with a Wittig-type reaction, i.e., the addition of a ylide to a carbonyl. Ylides for this reaction may be formed from phosphoranes or phosphonates. In the current invention, addition with a phosphonate ylide is preferred, this type of reaction is known as Wadsworth-Emmons reaction (see: "Advanced Organic Chemistry", March, J. Ed., 3rd Ed., John Wiley & Sons, New York, Chapter 16, p. 845–850, or Wadsworth, *Org. React.*, 25, p. 73–253 (1977)).

In this reaction a triester of a phosphonoalkylacid is treated with a strong base to abstract the proton alpha to the phosphonate, thus forming the phosphono ylide. In the current invention, the triester phosphonoalkyl acid were the triethylesters of phosphonoacetic acid or phosphonopropionic acid, although other esters may be used (see: Arbuzov, *Pure Appl. Chem.*, 9, p. 307–335 (1964)). Strong bases used to abstract the proton may be bases such as Li, Na, NaH, n-BuLi, etc., solvents for this reaction must be inert to the reaction conditions, such as, THF, ether, etc. Generally, these reactions are run at low temperature, $-30°$ to $-70°$ C. The stereochemical outcome for the double bond produced in this reaction is discussed in the above references. In general, the predominant isomer is the trans (Z) isomer; however, the other isomer may be isolated by chromatographic techniques. The current invention envisions either isomer and/or their mixture as novel and useful discoveries.

Other compounds of the present invention are prepared from the compounds of formula 1a by several routes. The double bond in linking group $X^a$ of compounds 1a may be reduced to the alkane in the presence of the carbonyl linking group, $Y^a$, with catalytic hydrogenation. For example, a compound of formula 1a is reduced with $H_2$ and 5% Pd/C in a solvent such as EtOH or EtOAc at ambient temperatures in 4–24 hours.

Alternatively, a compound of formula 1a is hydrolyzed to the corresponding carboxylic acid ($R^4$ is —OH) with either acid or base, followed by the reduction of the double bond. The reduction-hydrolysis sequence may be done in any order. The hydrolysis is accomplished with acid, such as, 5N HCl, 1N $H_2SO_4$, 1N HCl, etc. or with base, such as, 5N KOH, 1N NaOH, 2N LiOH, etc., at temperatures from $30°–100°$ C. in 4–24 hours.

Compounds of the present invention in which Y is carbonyl and $R^4$ is 1-piperidinyl, 1-pyrrolidinyl, methyl-1-pyrrolidinyl, dimethyl-1-pyrrolidino, 4-morpholino, dimethylamino, diethylamino, diisopropylamino, or 1-hexamethyleneimino are prepared by amidation or conversion of the esters to the corresponding amide. Such transformations are well known in the art of organic chemistry.

The carboxylic acids may be converted to an activated form, such as, an acid chloride, an acid azide, a mixed anhydride, hydroxysuccinimide, hydroxybenzotriazole, etc. Carboxylic acids may be dehydrated in the presence of an amine or alcohol to form the corresponding amides or ester with reagents, such as, DCC and the like.

Compounds of the present invention where Y is absent, X is alkylene, —$CH_2CH=CH$—, or —$CH_2CH_2CH=CH$— where $R^4$ is a nitrogen containing moiety and Y is a methylene, i.e., $R^4$ and Y constitute an amino function, are synthesized from the compounds corresponding amides by reduction of the amide carbonyl. This reduction may be accomplished with the use of reducing reagents, such as, $NaBH_4$, $LiAlH_4$, borane, and the like, in an inert solvent such as, THF, ether, $CH_2Cl_2$, etc., at ambient temperatures.

Reduction of any unsaturation in the linking group, X, is accomplished by techniques well know in the art such as catalytic reduction under hydrogen in the presence of a transition metal catalyst such as palladium, or platinum.

It should be noted that as before the reduction of the vinyl double (X) and the reduction of the carbonyl (Y) are independent of each other, i.e., there is no sequence restriction. Thus, an amine function can be synthesized before the reduction of the vinyl double or after.

Further, preferred compounds of formula I may be obtained by cleaving the $R^5$ and $R^6$ hydroxy protecting groups of formula Ia,b,c,e,f compounds via well known procedures. Numerous reactions for the formation and removal of such protecting groups are described in a number of standard works including, for example, Protective Groups in *Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for removing preferred $R^5$ and/or $R^6$ hydroxy protecting groups, particularly methyl, are essentially as described in Example 7, infra.

Other preferred compounds of formula I are prepared by replacing the 6-, -3' and/or 4'-position hydroxy moieties, when present, with a moiety of the formula —O—CO—($C_1$–$C_6$ alkyl), or —O—$SO_2$—($C_2$–$C_6$ alkyl) via well known procedures. See, e.g., U.S. Pat. No. 4,358,593.

For example, when an —O—CO($C_1$–$C_6$ alkyl) group is desired, a mono-, di-, or trihydroxy compound of formula I is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as atriethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, e.g., Haslam, et al., *Tetrahedron*, 36:2409–2433 (1980).

The reactions are carried out at moderate temperatures, in the range from about $-25°$ C. to about $100°$ C., frequently under an inert atmosphere such as nitrogen gas. However, ambient temperature is usually adequate for the reaction to run.

Acylation of a 6-, -3' and/or 4'-position hydroxy group also may be performed by acid-catalyzed reactions of the appropriate carboxylic acids in inert organic solvents. Acid catalysts such as sulfuric acid, polyphosphoric acid, methanesulfonic acid, and the like are used.

The aforementioned $R^1$ and/or $R^2$ groups of formula I compounds also may be provided by forming an active ester of the appropriate acid, such as the esters formed by such known reagents as dicyclohexylcarbodiimide(DCC), acylimidazoles, nitrophenols, pentachlorophenol, N-hydroxysuccinimide, and 1-hydroxybenzotriazole. See, e.g., *Bull. Chem. Soc. Japan*, 38:1979 (1965), and *Chem. Ber.*, 788 and 2024 (1970).

Each of the above techniques which provide —O—CO—($C_1$–$C_6$ alkyl) moieties are carried out in solvents as discussed above. Those techniques which do not produce an acid product in the course of the reaction, of course, do not call for the use of an acid scavenger in the reaction mixture.

When a formula I compound is desired in which the 6-,-3' and/or 4'-position hydroxy group of a formula I compound is converted to a group of the formula —O—SO$_2$—(C$_2$-C$_6$ alkyl), the mono-, di-, or trihydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). Such reactions are carried out under conditions such as were explained above in the discussion of reaction with acid halides and the like.

Although the free-base or acid forms of formula I compounds can be used in the methods of the present invention, it is preferred to prepare and use a pharmaceutically acceptable salt form. Thus, the compounds used in the methods of this invention form pharmaceutically acceptable acid or base addition salts with a wide variety of organic and inorganic acids and bases, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, b-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. Preferred salts are the hydrochloride and oxalate salts.

Typical bases used to form pharmaceutically acceptable addition salts would be inorganic bases, such as, sodium hydroxide, potassium hydroxide, alkali carbonates or bicarbonates, calcium carbonate, magnesium carbonate, and the like. Additionally, organic bases may be utilized to form addition salts, e.g., alkyl amines, such as, triethylamine, dimethylamine, i-propylamine, and the like The pharmaceutically acceptable acid or base addition salts are typically formed by reacting a compound of formula I with an equimolar or excess amount of acid or base. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

The term "solvate" represents an aggregate that comprises one or more molecules of the solute, such as a formula I compound, with one or more molecules of solvent The following examples are presented to further illustrate the preparation of compounds of the present invention. The Examples are merely illustrative and are not to be read as limiting the scope of the present invention as it is defined by the appended claims.

NMR data for the following Examples were generated on a GE 300 MHz NMR instrument, and anhydrous d-6 DMSO was used as the solvent unless otherwise indicated.

PREPARATION 1

Preparation of 2-(4-methoxyphenyl)-4-(3-methoxyphenyl)butyric acid

4-Methoxyphenylacetic acid (50.68 g, 305 mmol) was dissolved in 1.4 L of THF and cooled to −70° C. under a nitrogen atmosphere. 400 mL of 1.6M (640.5 mmol) of n-BuLi in hexane was slowly added. 72.1 g (335.5 mmol) of 2-(3-methoxyphenyl)ethylbromide in 400 mL of THF was slowly added and the reaction allowed to proceed for 1.5 hours. The reaction was allowed to warm to ambient temperature. The reaction was quenched with 500 mL of 0.5N NaOH and heated to 50° C. for one hour and cooled to ambient temperature. The reaction mixture was extracted three times with ether, the aqueous layer was acidified with 150 mL of 5N HCl and extracted twice with CHCl$_3$. The CHCl$_3$ extract was washed twice with brine, dried with Na$_2$SO$_4$, and evaporated to a yellow solid. This yielded 78.2 g of the title compound.

$^1$H NMR: Consistent with the proposed stucture. MS: m/e=300 (M) FD Analysis: Calc. for C$_{18}$H$_{20}$O$_4$: C, 71.98; H, 6.71 Fd: C, 71.04; H, 6.77

PREPARATION 2

Preparation of 2-(4-Methoxyphenyl)-6-methoxy-1-tetralone 2-(4-Methoxyphenyl)-4-(3-methoxyphenyl)butric acid (2.31 g, 7.7 mmol) was dissolved in 30 mL of CH$_2$Cl$_2$ and cooled to 0° C. To this solution was added 3.4 ml (23.1 mmol) of trifluoroacetic acid, the reaction was allowed to proceed for 30 minutes. The reaction was quenched by pouring into an aqueous solution of NaHCO$_3$. The organic layer was separated, washed twice with NaHCO$_3$ solution, washed twice with brine, dried with Na$_2$SO$_4$, and evaporated to a solid. This yielded 1.5 g of the title compound as a tan amorphous solid.

PREPARATION 3

Preparation of 2-(4-methoxyphenyl)-6-methoxy-1-naphthol 2-(4-Methoxyphenyl)-6-methoxy-1-tetralone (8.50 g, 30.14 mmol) was dissolved in 50 mL of isopropenyl acetate and 1 g of para-toluenesulfonic acid was added. The reaction mixture heated to reflux under a nitrogen atmosphere for six hours. The reaction mixture was allowed to cool to ambient temperature, 2,3-dichloro-5,6-dicyano-1,4-benzoquinone (DDQ), 13.7 g (60.3 mmol) was added. The reaction was refluxed for 1.5 hours, after cooling to ambient temperature, 200 mL of CH$_2$Cl$_2$ was added. The reaction mixture was washed four times with 200 mL portions of 0.2N NaOH, twice with 200 mL portions of water, and the resulting solution was dried with Na$_2$SO$_4$ and evaporated to a solid.

This yielded the intermediate phenolic acetate which was hydroyzed by dissolving the solid in 200 mL of MeOH-THF (1:1) (v/v) and added an excess amount of MeONa. An orange precipitate formed which was filtered off. The resulting filtrate was acidified with to pH 4 with 5N HCl and diluted with 200 mL of water. The solution was extracted three times with 100 mL portions of EtOAc and organic layers combind, dried with $Na_2SO_4$, evaporated to dryness. The final product was crystallized from EtOAc-hexane, which yielded 4.24 g of the title compound as a white solid.

$^1$H NMR: Consistent with the proposed structure.

MS: M/e=280 (M)FD Analysis: Calc. for $C_{18}H_{16}O_3$: C, 77.12; H, 5.75 Fd: C, 76.83; H, 5.90

PREPARATION 4

Preparation of 2-(3-methoxyphenyl)-6-methoxy-1-tetralone

In a manner similar to that used in Preparation 2, the title compound was prepared as a tan solid, mp 81–82_C.

PREPARATION 5

Preparation of 1-hydroxy-2-(3-methoxyhenyl)-6-methoxynaphthalene

In a manner similar to that used in Preparation 3, the title compound was prepared as a clear oil.

$^1$H NMR: (CDCl$_3$) 8.19 ppm (d, J=9.1 Hz, 1H); 7.51–6.94 ppm (m, 8H); 5.91 ppm (s, 1H); 3.94 ppm (s, 3H) MS: m/e=280 (M) FD Analysis: Calc. for $C_{18}H_6O_3$: C, 77.12; H, 5.75 Found: C, 76.91; H, 5.81.

PREPARATION 6

Preparation of 1-hydroxy-2-(3-methoxyphenyl)naphthalene

In a manner analogous to Preparations 1–3, the title compound was prepared as a tan, amorphous solid.

$^1$H NMR: 8.30 ppm (m, 1H); 7.80 ppm (m, 1H); 7.57–7.45 ppm (m, 4H); 7.40 ppm (d, J=7.1 Hz, 1); 7.35 ppm (d, J=6.0 Hz, 1H); 7.06 ppm (s, 1H0; 6.97 ppm (dd, J=6.0 Hz, 1H); 6.00 ppm (s, 1H); 3.90 ppm (s, 1H) MS: m/e=250 (M) FD Analysis: Calc. for $C_{17}H_{14}O_2$—0.21 mol EtOAc: C, 79.52; H, 5.93 Found: C, 79.72; H, 5.63

PREPARATION 7

1-(4-formylphenoxy)-2-(4-methoxyphenyl)-6-methoxynaphthalene

To a solution of [2-(4-methoxyphenyl)]-6-methoxynaphthyl-1-ol (3.57 g, 12.75 mmol) in 180 mL of anhydrous N,N-dimethylformamide under N$_2$ at ambient temperature was added sodium hydride (535 mg, 13.38 mmol, 60% dispersion in mineral oil) in small portions. After stirring for 10 min., 4-flourobenzaldehyde (3.20 g, 25.50 mmol) was added. The resulting mixture was heated to 70° C. for 36 hours. Upon cooling to ambient temperature, the solvent was removed in vacuo. The residue was then distributed between ethyl acetate/water. The layers were separated and the organic was washed several times with water. The organic layer was finally dried (sodium sulfate) and concentrated in vacuo to an oil. Chromatography (90:10 hexanes/ethyl acetate) provided 2.06 g (48%) of 1-(4-formyl)phenoxy-2-(4-methoxyphenyl)-6-methoxynaphthalene as a white solid that was crystallized from methanol. Data for 1-(4-formyl)phenoxy-2-(4-methoxyphenyl)-6-methoxynaphthalene: mp 120–121° C.

$^1$H NMR (CDCl$_3$) d 9.80 (s, 1H), 7.78 (d, J=9.2 Hz, 1H), 7.74 (d, J=8.8 Hz, 1H), 7.67 (d, J=8.8 Hz, 2H), 7.56 (d, J=8.8 Hz, 1H), 7.46 (d, J=8.8 Hz, 2H), 7.21 (d, J=2.6 Hz, 1H), 7.12 (dd, J=9.2, 2.6 Hz, 1H), 6.84 (d, J=8.8 Hz, 2H), 6.81 (d, J=8.8 Hz, 2H), 3.95 (s, 3H), 3.78 (s, 3H). FD mass spec: 384. Anal. Calcd. for $C_{25}H_{20}O_4$: C, 78.11; H, 5.24. Found: C, 78.32; H, 5.24.

PREPARATION 8

Preparation of 1-(4-formylphenoxy)-2-(3-methoxyphenyl)-6-methoxynaphthalene

A solution was prepared of 9.8 g (35 mmol) of 1-hydroxy-2-(3-methoxyphenyl)-6-methoxynaphthalene in 490 mL of DMF under a nitrogen atmosphere and to this solution was slowly added 1.47 g (36.8 mmol) of 60% NaH in mineral oil. After ten minutes, 7.5 mL (70 mmol) of 4-fluorobenzaldehdye was added and the reaction mixture was heated to 70° C. for sixty-four hours. The reaction mixture was evaporated to dryness and the residue partioned between water and EtOAc. The EtOAc layer was dried with Na$_2$SO$_4$ and chromatographed on a silica gel column eluted with EtOAc-hexane (1:9)(v/v). The final product was further purified by crystallization from MeOH. This yielded 2.4 g of the title compound as a tan solid, mp 145–146° C.

$^1$H NMR: (CDCl$_3$) 9.80 ppm (s, 1H); 7.79 ppm (d, J=9.2 Hz, 1H); 7.75 ppm (d, J=8.8 Hz, 1H); 7.67 ppm (d, J=8.9 Hz, 2H); 7.58 ppm (d, J=8.4 Hz, 1H); 7.31–7.05 ppm (m, 5H); 6.86–6.75 ppm (m, 3H); 3.95 ppm (s, 3H); 3.72 ppm (s, 3H) MS: m/e=384 (M) FD Analysis: Calc. for $C_{25}H_{20}O_4$: C, 78.11; H, 5.24 Found: C, 78.26; H, 5.33

PREPARATION 9

Preparation of 1-(4-formylphenoxy)-2-(3-methoxyphenyl)naphthalene

In a manner similar to that used in Preparation 7, the title compound was prepared.

$^1$H NMR: (CDCl$_3$) 9.90 ppm (s, 1H); 7.90–7.83 ppm (m,2H); 7.70 ppm (d, J=8.0 Hz, 1H); 7.35–7.20 ppm (m, 4H); 7.58–7.43 ppm (m, 2H); 7.58 ppm (d, J=8.4 Hz, 1H); 7.10 ppm (m, 2H); 6.80 ppm (d, J=8.0 Hz, 2H); 3.80 ppm (s, 3H) MS: m/e=354 (M) FD Analysis: Calc. for $C_{24}H_{18}O_3$—0.2 mol EtOAc: C, 86.06; H, 5.31 Found: C, 80.17; H, 5.29

EXAMPLE 1

Preparation of 3-[4-(2-(4-methoxyphenyl)-6-methoxynaphth-1-yloxy)phenyl]propenoic acid, ethyl ester

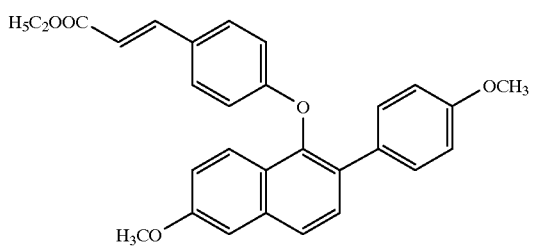

A solution was prepared of 495 mg (2.2 mmol) of triethylphosphonoacetate in 10 mL of anhydrous tetrahydrofuran. The solution was cooled to −70° C. and 1.4 mL of 1.6M n-BuLi in hexane (2.2 mmol) was added and allowed to stir for ten minutes at −700 under a nitrogen atmosphere. A solution of 696 mg (2 mmol) of 1-(4-formylphenoxy)-2-(4-methoxyphenyl)-6-methoxynaphthalene in 10 mL of THF was dropwise added to the phosphoylide. The reaction mixture was allowed to warm slowly to ambient temperature. After one hour, the reaction was examined by thin-layer chromatography for completion, and the reaction was again cooled to −60° C. and an additional 50 mg of triethylphosphonoacetate and 1.4 mL of 1.6M n-BuLi in hexane was added. The reaction was allowed to warm to ambient temperature. After two hours, the reaction was quenched with water and extracted three times with ethyl acetate. The combined ethyl acetate extracts were washed with brine, dried with $Na_2SO_4$, and evaporated to dryness. The compound was further purified by chromatography on a silica gel column eluted with a linear gradient beginning with EtOAc-hexane (3:97) (v/v) and ending with EtOAc-hexane (10:90) (v/v). This yielded 786 mg of the title compound as an tan amorphous solid, mp 94–97° C.

$^1$H NMR: Consistent with the proposed structure. MS: m/e=454 (M) FD Analysis: Calc. for $C_{29}H_{26}O_5$: C, 76.63; H, 5.77 Found: C, 76.43; H, 5.94.

EXAMPLE 2

Preparation of 3-[4-((2-(4-methoxyphenyl)-6-methoxynaphth-1-yl)oxy)phenyl]propenoic acid, hydrate

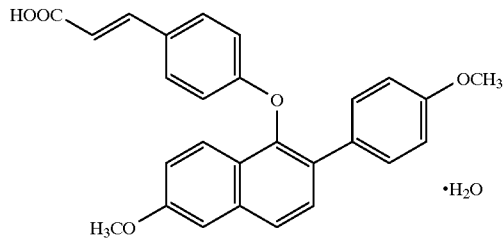

A solution was prepared of 771 mg (1.7 mmol) of 3-[4-((2-(4-methoxyphenyl)-6-methoxynaphth-1-yl)oxy) phenyl]propenoic acid, ethyl ester (prepared as described in Example 1 above) in 10 mL of ethanol, 7 mL of tetrahydrofuran, and 10 mL of 1N NaOH. The reaction was warmed on a steam bath to clearify the solution. After one hour, an additional 2 mL of 2N NaOH was added and the reaction was warmed. The reaction was quenched by addition of cold 2N HCl. The aqueous mixture was extracted three times with ether. The combined ether extracts were washed with brine, dried with $Na_2SO_4$, and evaporated to dryness. The product was purified by chromatography on a silica gel column eluted with MeOH—$CHCl_3$ (1:99) (v/v). This yielded 704 mg of the title compound as a tan amorphous solid. mp 97–100° C.

$^1$H NMR: Consistent with the proposed structure. MS: m/e=426 (M) FD Analysis: Calc. for $C_{27}H_{22}O_5$—HOH: C, 72.96; H, 5.44 Found: C, 73.03; H, 5.20.

EXAMPLE 3

Preparation of 3-[4-((2-(4-hydroxyphenyl)-6-hydroxynaphth-1-yl)oxy)phenyl]propenoic acid

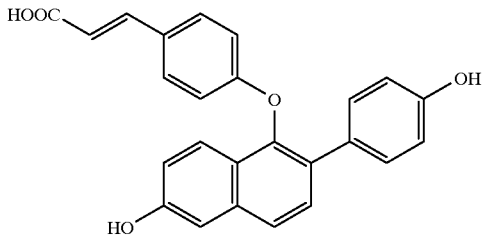

A solution was prepared of 658 mg (1.54 mmol) of 3-[4-((2-(4-methoxyphenyl)-6-methoxynaphth-1-yl)oxy) phenyl]propenoic acid hydrate in 10 mL of dichloromethane. The solution was cooled to 5° C. and 0.44 mL (4.7 mmol) of $BBr_3$ was added. The reaction was allowed to proceed for one hour at 0° C. under a nitrogen atmosphere. The reaction was quenched by pouring into water and extracting three times with ethyl acetate. The combined ethyl acetate extracts were washed with water, brine, dried with $Na_2SO_4$, and evaporated to an oily, red solid. The product was purified by chromatography on a silica gel column eluted with MeOH—$CHCl_3$ (1:99) (v/v). This yielded 489 mg of the title compound as a yellow, amorphous solid, mp 150–153° C.

$^1$H NMR: Consistent with the proposed structure. MS: m/e=398 (M) FD Analysis: Calc. for $C_{25}H_{18}O_5$: C, 75.37; H, 4.55 Found: C, 75.64; H, 4.65.

EXAMPLE 4

Preparation of 3-[4-((2-(4-methoxyphenyl)-6-methoxynaphth-1-yl)oxy)phenyl]propenoic acid, piperidinamide

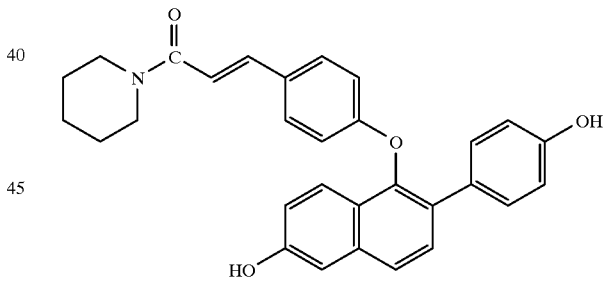

A solution was prepared of 1.04 g (2.4 mmol) of 3-[4-((2-(4-methoxyphenyl)-6-methoxynaphth-1-yl)oxy)phenyl] propenoic acid, 356 mg (2.64 mmol) of 1-hydroxybenzotriazole, and 204 mg (2.4 mmol) of piperidine in 20 mL of DMF. To this solution was added 550 mg (2.64 mmol) of dicyclohexylcabodiimide (DCC). The reaction was allowed to proceed for sixteen hours at ambient temperature under a nitrogen atmosphere. The reaction was terminated and 50 mL of ethyl acetate was added and the suspension filtered. The organic solution was washed four times with water, brine, dried with $Na_2SO_4$, and evaporated to dryness. The product was purified by chromatography on a silica gel column eluted with $CHCl_3$ to yield 662 mg of the title compound as a white amorphous solid.

$^1$H NMR: Consistent with the proposed structure. MS: m/e=493 (M) FD Analysis: Calc. for $C_{32}H_{31}NO_4$: C, 77.87; H, 6.33; N, 2.84 Found: C, 75.08; H, 6.43; N, 4.09.

EXAMPLE 5

Preparation of 1-[4-(3-(1-Piperidinyl)prop]-2-enyl)phenoxyl-2-(4-methoxyphenyl)-6-methoxynaphthalene

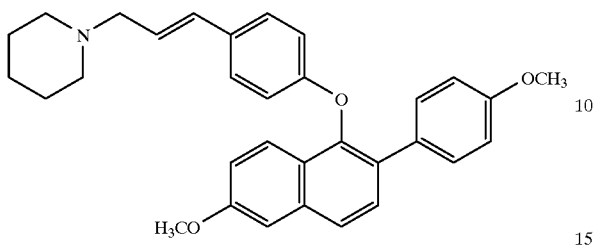

A suspension was prepared of 255 mg (6.7 mmol) of LiAlH$_4$ in 5 mL of THF. To this solution was added, dropwise, 660 mg (1.34 mmol) of 3-[4-((2-(4-methoxyphenyl)-6-methoxynaphth-1-yl)oxy)phenyl]propenoic acid piperidinamide in 15 mL of tetrahydrofuran. The reaction mixture was heated under reflux for three hours under a nitrogen atmosphere. The reaction was quenched by pouring into ice-water. The suspension was extracted three times with ethyl acetate. The combined extracts were washed with brine, dried with Na$_2$SO$_4$, and evaporated to dryness, yielding 541 mg of the crude product. Final purification was accomplished by chromatography to yield 891 mg of crude material. This was chromatographed on a silica gel column eluted with a stepwise gradient of MeOH—CHCl$_3$ (1:99), (5:95), and (10:90) (v/v). to yield 483 mg of the title compound, isolated as a tan amorphous solid.

$^1$H NMR: Consistent with the proposed structure. MS: m/e=479 (M) FD.

EXAMPLE 6

Preparation of 1-[4-[3-(1-Piperidinyl)propyl]phenoxy]-2-(4-methoxyphenyl)-6-methoxynaphthalene Hydrochloride

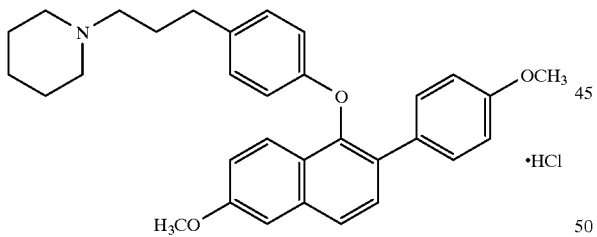

A solution was prepared of 470 mg (1 mmol) of 1-[4-[3-(1-piperidinyl)2-propenyl]phenoxy]-2-(4-methoxyphenyl)-6-methoxynaphthalene (prepared as described in Example 5 above) in 25 mL of ethyl acetate and 75 mL of ethanol. To this solution was added 480 mg of 5% Pd/C, and the mixture was placed in a Parr hydrogenation apparatus under H$_2$ at a pressure of 4 psi. After one hour, the reaction mixture was filtered to remove the catalyst and the residue was evaporated to dryness. The residue was dissolved in 10 mL of ethyl acetate and ether saturated with HCl was added until no further precipitate formed. The solvents were removed by evaporation. This yielded 429 mg of the title compound as a white amorphous solid, mp 192–194° C.

$^1$H NMR: Consistent with the proposed structure. MS: m/e=481 (M—HCl) FD 20 Analysis: Calc. for C$_{32}$H$_{35}$NO$_3$—HCl: C, 74.19; H, 7.00; N, 2.70 Found: C, 73.90; H, 6.95; N, 2.72.

EXAMPLE 7

Preparation of 1-[4-[3-(1-Piperidinyl)propyl]phenoxyl]-2-(4-hydroxyphenyl)-6-hydroxynaphthalene Hydrochloride

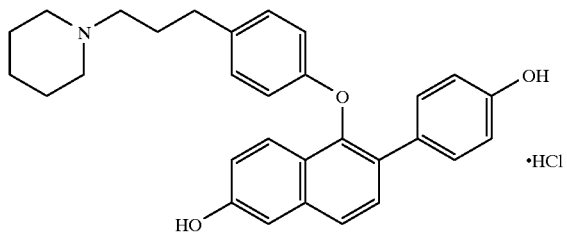

A solution of 315 mg (0.61 mmol) of 1-[4-[3-(1-piperidinyl)2-propyl]phenoxy]-2-(4-methoxyphenyl)-6-methoxynaphthalene hydrochloride (prepared as described in Example 7 above) in 20 mL of dichloromethane was prepared, cooled to 5° C., and 0.17 mL (1.83 mmol) of BBr$_3$ was added. The reaction was allowed to proceed at 5° C. under a nitrogen atmosphere for thirty minutes. The reaction was quenched by pouring into a saturated solution of aqueous NaHCO$_3$ The aqueous suspension was extracted with CH$_2$Cl$_2$ five times. The combined CH$_2$Cl$_2$ extract was washed with brine, dried with Na$_2$SO$_4$, and evaporated to dryness. The residue was dissolved in EtOAc-EtOH and diethyl ether, saturated with HCl, was added until no further precipitate formed. This yielded 271 mg of the title compound as a white solid, mp 222–224° C.

$^1$H NMR: Consistent with the proposed structure. MS: m/e=454 (M—Cl) FD Analysis: Calc. for C$_{30}$H$_{31}$NO$_3$—HCl: C, 73.53; H, 6.58; N, 2.86 Found: C, 73.75; H, 6.49; N, 2.92.

We claim:
1. A compound of formula 1

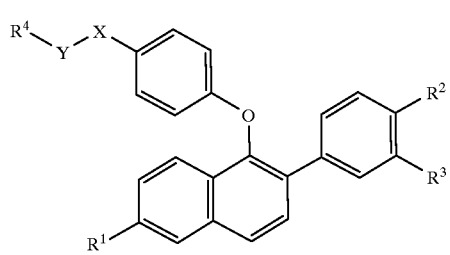

or a pharmaceutically acceptable salt thereof wherein
R$^1$ is selected from the group consisting of
  hydrogen,
  hydroxy,
  alkoxy of one to four carbon atoms,
  alkoxycarbonyl of two to seven carbon atoms,
  alkoxycarbonyloxy of two to seven carbon atoms,
  alkylsulfonyloxy,
  phenoxycarbonyloxy, and
  aryloxycarbonyl where the aryl portion is selected from the group consisting of
    unsubstituted phenyl, and
    phenyl substituted with one or more substituents independently selected from the group consisting of halo,
methyl,
methoxy,
nitro, and
trifluoromethyl;

$R^2$ and $R^3$ are, independently selected from the group consisting of
hydrogen,
chloro,
fluoro,
hydroxy,
alkoxy of one to four carbon atoms,
alkoxycarbonyl of two to seven carbon atoms,
alkoxycarbonyloxy of two to seven carbon atoms,
alkylsulfonyloxy,
phenoxycarbonyloxy, and
aryloxycarbonyl where the aryl portion is selected from the group consisting of
unsubstituted phenyl, and
phenyl substituted with one or more substituents independently selected from the group consisting of
halo,
methyl,
methoxy,
nitro, and
trifluoromethyl;

$R^4$ is selected from the group consisting of
hydroxy,
alkoxy of one to six carbon atoms,
cycloalkoxy of four to six carbon atoms,
1-piperidinyl,
1-pyrrolidinyl,
methyl-1-pyrrolidinyl,
dimethyl-1-pyrrolidino,
4-morpholino,
dimethylamino,
diethylamino,
diisopropylamino,
1-hexamethyleneimino, and
aryloxy where wherein the aryl portion is selected from the group consisting of
unsubstituted phenyl, and
phenyl substituted with one or more substituents independently selected from the group consisting of
halo,
methyl,
methoxy,
nitro, and
trifluoromethyl;

X is selected from the group consisting of
alkylene of two to four carbon atoms,
—CH=CH—,
—CH$_2$CH=CH—, and
—CH$_2$CH$_2$CH=CH—; and Y is absent or is carbonyl, with the proviso that when Y is absent, $R^4$ may not be hydroxy, —O(C$_1$–C$_6$ alkyl), —O(C$_4$–C$_6$ cycloalkyl), or —OAr.

2. A compound as defined by claim 1 having the structure wherein $R^1$, $R^2$, $R^3$, and $R^4$ and X are as defined therein.

3. A compound as defined by claim 1 having the structure wherein $R^1$, $R^2$, $R^3$, and $R^4$ and X are as defined therein.

4. A compound according to claim 3 wherein $R^4$ is selected from the group consisting of
hydroxy,
—O(C$_1$–C$_6$ alkyl),
—O(C$_4$–C$_6$ cycloalkyl),
—OAr where where Ar is unsubstituted phenyl or is phenyl substituted with one or more substituents independently selected from the group consisting of
halo,
nitro,
trifluoromethyl,
methyl, and
methoxy.

5. A compound according to claim 4 selected from the group consisting of
3-[4-(2-phenyl-6-hydroxynaphth-1-yloxy)phenyl] propenoic acid;
3-[4-(2-phenyl-6-methoxynaphth-1-yloxy)phenyl] propenoic acid;
3-[4-(2-(4-chlorophenyl)naphth-1-yloxy)phenyl] propenoic acid;
3-[4-(2-(3-chloro-4-methoxyphenyl)naphth-1-yloxy) phenyl]propenoic acid;
3-[4-(2-(3-chloro-4-hydroxyphenyl)naphth-1-yloxy) phenyl]propenoic acid;
3-[4-(2-(4-hydroxyphenyl)naphth-1-yloxy)phenyl]- propenoic acid;
3-[4-(2-(4-methoxyphenyl)naphth-1-yloxy)phenyl]- propenoic acid;
3-[4-(2-(3-chlorophenyl)-6-hydroxynaphth-1-yloxy) phenyl]propenoic acid;
3-[4-(2-(3-chlorophenyl)-6-methoxynaphth-1-yloxy) phenyl]propenoic acid;
3-[4-(2-(4-chlorophenyl)-6-hydroxynaphth-1-yloxy) phenyl]propenoic acid;
3-[4-(2-(4-chlorophenyl)-6-methoxynaphth-1-yloxy) phenyl]propenoic acid;

3-[4-(2-(4-hydroxyphenyl)-6-hydroxynaphth-1-yloxy)
phenyl]propenoic acid;
3-[4-(2-(4-methoxyphenyl)-6-hydroxynaphth-1-yloxy)
phenyl]propenoic acid;
3-[4-(2-(4-methoxyphenyl)-6-methoxynaphth-1-yloxy)
phenyl]propenoic acid;
4-[4-(2-(4-fluorophenyl)-6-hydroxynaphth-1-yloxy-
phenyl]but-3-enoic acid;
4-[4-(2-(4-fluorophenyl)-6-methoxynaphth-1-yloxy)
phenyl]but-3-enoic acid;
4-[4-(2-(4-hydroxyphenyl)naphth-1-yloxy)phenyl]but-3-
enoic acid;
4-[4-(2-(4-methoxyphenyl)naphth-1-yloxy)phenyl]but-3-
enoic acid;
4-[4-(2-(3-chloro-4-hydroxyphenyl)naphth-1-yloxy)
phenyl]but-3-enoic acid;
4-[4-(2-(3-chloro-4-methoxyphenyl)naphth-1-yloxy)
phenyl]but-3-enoic acid;
4-[4-(2-(4-hydroxyphenyl)-6-hydroxynaphth-1-yloxy)
phenyl]but-3-enoic acid;
4-[4-(2-(4-methoxyphenyl)-6-hydroxynaphth-1-yloxy)
phenyl]but-3-enoic acid;
4-[4-(2-(4-methoxyphenyl)-6-methoxynaphth-1-yloxy)
phenyl]but-3-enoic acid;
4-[4-(2-phenyl)naphth-1-yloxy)phenyl]but-3-enoic acid
3-[4-(2-phenyl-6-hydroxynaphth-1-yloxy)phenyl]
propenoic acid;
3-[4-(2-phenyl-6-methoxynaphth-1-yloxy)phenyl]
propenoic acid;
3-[4-(2-(3-hydroxyphenyl)-6-hydroxynaphth-1-yloxy)
phenyl]propanoic acid;
3-[4-(2-(3-methoxyphenyl)-6-hydroxynaphth-1-yloxy)
phenyl]propanoic acid;
3-[4-(2-(3-methoxyphenyl)-6-methoxynaphth-1-yloxy)
phenyl]propanoic acid;
3-[4-(2-(4-hydroxyphenyl)-6-hydroxynaphth-1-yloxy)
phenyl]propanoic acid;
3-[4-(2-(4-methoxyphenyl)-6-hydroxynaphth-1-yloxy)
phenyl]propanoic acid;
3-[4-(2-(4-methoxyphenyl)-6-methoxynaphth-1-yloxy)
phenyl]propanoic acid;
3-[4-(2-(4-chlorophenyl)-6-hydroxynaphth-1-yloxy)
phenyl]propanoic acid;
3-[4-(2-(4-chlorophenyl)-6-methoxynaphth-1-yloxy)
phenyl]propanoic acid;
3-[4-(2-(3-fluorophenyl)-6-hydroxynaphth-1-yloxy)
phenyl]propanoic acid;
3-[4-(2-(3-fluorophenyl)-6-methoxynaphth-1-yloxy)
phenyl]propanoic acid;
4-[4-(2-(4-hydroxyphenyl)-6-hydroxynaphth-1-yloxy)
phenyl]butanoic acid;
4-[4-(2-(4-methoxyphenyl)-6-hydroxynaphth-1-yloxy)
phenyl]butanoic acid; and
4--[4-(2-(4-methoxyphenyl)-6-methoxynaphth-1-yloxy)
phenyl]butanoic acid; or
a pharmaceutically acceptable salt thereof.
6. A compound according to claim 4 selected from the
group consisting of
3-[4-(2-(3-hydroxyphenyl)-6-hydroxynaphth-1-ylyloxy)
phenyl]propenoic acid, ethyl ester;
3-[4-(2-(3-methoxyphenyl)-6-methoxynaphth-1-yloxy)
phenyl]propenoic acid, ethyl ester;
3-[4-(2-(4-hydroxyphenyl)-6-hydroxynaphth-1-yloxy)
phenyl]propenoic acid, ethyl ester;
3-[4-(2-(4-methoxyphenyl)-6-hydroxynaphth-1-yloxy)
phenyl]propenoic acid, ethyl ester;
3-[4-(2-(3-hydroxyphenyl)-6-hydroxynaphth-1-yloxy)
phenyl]propenoic acid, propyl ester;
3-[4-(2-(3-methoxyphenyl)-6-methoxynaphth-1-yloxy)
phenyl]propenoic acid, propyl ester;
3-[4-(2-(4-hydroxyphenyl)-6-hydroxynaphth-1-yloxy)
phenyl]propenoic acid, butyl ester;
3-[4-(2-(4-methoxyphenyl)-6-methoxynaphth-1-yloxy)
phenyl]propenoic acid, butyl ester;
3-[4-(2-(3-hydroxyphenyl)-6-hydroxynaphth-1-yloxy)
phenyl]propenoic acid, pentyl ester;
3-[4-(2-(3-methoxyphenyl)-6-methoxynaphth-1-yloxy)
phenyl]propenoic acid, pentyl ester;
3-[4-(2-(4-hydroxyphenyl)-6-hydroxynaphth-1-yloxy)
phenyl]propenoic acid, hexyl ester;
3-[4-(2-(4-methoxyphenyl)-6-methoxynaphth-1-yloxy)
phenyl]propenoic acid, hexyl ester;
3-[4-(2-(3-hydroxyphenyl)naphth-1-yloxy)phenyl]-
propenoic acid, ethyl ester;
3-[4-(2-(3-methoxyphenyl)naphth-1-yloxy)phenyl]-
propenoic acid, ethyl ester;
3-[4-(2-(4-hydroxyphenyl)naphth-1-yloxy)phenyl]-
propenoic acid, ethyl ester;
3-[4-(2-(4-methoxyphenyl)naphth-1-yloxy)phenyl]-
propenoic acid, ethyl ester;
3-[4-(2-phenylnaphth-1-yloxy)phenyl]propenoic acid,
ethyl ester;
3-[4-(2-(4-chlorophenyl)-6-hydroxynaphth-1-yloxy)
phenyl]propenoic acid, ethyl ester;
3-[4-(2-(4-chlorophenyl)-6-methoxynaphth-1-yloxy)
phenyl]propenoic acid, ethyl ester;
3-[4-(2-(3-fluorophenyl)-6-hydroxynaphth-1-yloxy)
phenyl]propenoic acid, ethyl ester;
3-[4-(2-(3-fluorophenyl)-6-methoxynaphth-1-yloxy)
phenyl]propenoic acid, ethyl ester;
3-[4-(2-(4-fluorophenyl)-6-hydroxynaphth-1-yloxy)
phenyl]propenoic acid, ethyl ester;
3-[4-(2-(4-fluorophenyl)-6-methoxynaphth-1-yloxy)
phenyl]propenoic acid, ethyl ester;
3-[4-(2-(3-fluoro-4-methoxyphenyl)-6-methoxynaphth-
1-yloxy)phenyl]propenoic acid, ethyl ester;
3-[4-(2-(3-fluoro-4-hydroxyophenyl)-6-hydroxynaphth-
1-yloxy)phenyl]propenoic acid, ethyl ester;
4-[4-(2-(3-fluorophenyl)naphth-1-yloxy)phenyl]but-3-
enoic acid, ethyl ester;
4-[4-(2-(4-hydroxyphenyl)-6-hydroxynaphth-1-yloxy)
phenyl]but-3-enoic acid, ethyl ester;
4-[4-(2-(4-methoxyphenyl)-6-methoxynaphth-1-yloxy)
phenyl]but-3-enoic acid, ethyl ester;
4-[4-(2-(4-hydroxyphenyl)-6-hydroxynaphth-1-yloxy)
phenyl]but-3-enoic acid, pentyl ester;
4-[4-(2-(4-methoxyphenyl)-6-methoxynaphth-1-yloxy)
phenyl]but-3-enoic acid, pentyl ester;
4-[4-(2-(4-hydroxyphenyl)-6-hydroxynaphth-1-yloxy)
phenyl]but-3-enoic acid, cyclohexyl ester;
4-[4-(2-(4-methoxyphenyl)-6-methoxynaphth-1-yloxy)
phenyl]but-3-enoic acid, cyclohexyl ester;
4-[4-(2-(4-hydroxyphenyl)naphth-1-yloxy)phenyl]but-3-
enoic acid, cyclohexyl ester;

4-[4-(2-(4-methoxyphenyl)naphth-1-yloxy)phenyl]but-3-enoic acid, cyclohexyl ester;

4-[4-(2-(4-hydroxyphenyl)-6-hydroxynaphth-1-yloxy)phenyl]but-3-enoic acid, phenyl ester;

4-[4-(2-(4-methoxyphenyl)-6-methoxynaphth-1-yloxy)phenyl]but-3-enoic acid, phenyl ester;

4-[4-(2-(4-hydroxyphenyl)-6-hydroxynaphth-1-yloxy)phenyl]but-3-enoic acid, 4-methylphenyl ester;

4-[4-(2-(4-methoxyphenyl)-6-methoxynaphth-1-yloxy)phenyl]but-3-enoic acid, 4-methylphenyl ester;

3-[4-(2-(3-hydroxyphenyl)naphth-1-yloxy)phenyl]-propanoic acid, ethyl ester;

3-[4-(2-(3-methoxyphenyl)naphth-1-yloxy)phenyl]-propanoic acid, ethyl ester;

3-[4-(2-(4-hydroxyphenyl)naphth-1-yloxy)phenyl]-propanoic acid, ethyl ester;

3-[4-(2-(4-methoxyphenyl)naphth-1-yloxy)phenyl]-propanoic acid, ethyl ester;

3-[4-(2-(3-hydroxyphenyl)-6-hydroxynaphth-1-yloxy)phenyl]propanoic acid, ethyl ester;

3-[4-(2-(3-methoxyphenyl)-6-methoxynaphth-1-yloxy)phenyl]propanoic acid, ethyl ester;

3-[4-(2-(3-hydroxyphenyl)-6-hydrxynaphth-1-yloxy)phenyl]propanoic acid, propyl ester;

3-[4-(2-(3-methoxyphenyl)-6-methoxynaphth-1-yloxy)phenyl]propanoic acid, propyl ester;

3-[4-(2-(3-hydroxyphenyl)-6-hydroxynaphth-1-yloxy)phenyl]propanoic acid, pentyl ester;

3-[4-(2-(3-methoxyphenyl)-6-methoxynaphth-1-yloxy)phenyl]propanoic acid, pentyl ester;

3-[4-(2-(3-fluorophenyl)-6-hydroxynaphth-1-yloxy)phenyl]propanoic acid, ethyl ester;

3-[4-(2-(3-fluorophenyl)-6-methoxynaphth-1-yloxy)phenyl]propanoic acid, ethyl ester;

3-[4-(2-(4-fluorophenyl)-6-hydroxynaphth-1-yloxy)phenyl]propanoic acid, ethyl ester;

3-[4-(2-(4-fluorophenyl)-6-methoxynaphth-1-yloxy)phenyl]propanoic acid, ethyl ester;

3-[4-(2-(3-fluoro-4-hydroxyphenyl)-6-hydroxynaphth-1-yloxy)phenyl]propanoic acid, ethyl ester;

3-[4-(2-(3-fluoro-4-methoxyphenyl)-6-methoxynaphth-1-yloxy)phenyl]propanoic acid, ethyl ester;

3-[4-(2-(4-chlorophenyl)-6-hydroxynaphth-1-yloxy)phenyl]propanoic acid, ethyl ester;

3-[4-(2-(4-chlorophenyl)-6-methoxynaphth-1-yloxy)phenyl]propanoic acid, ethyl ester;

3-[4-(2-(4-hydroxyphenyl)-6-hydroxynaphth-1-yloxy)phenyl]propanoic acid, ethyl ester;

3-[4-(2-(4-methoxyphenyl)-6-methoxynaphth-1-yloxy)phenyl]propanoic acid, ethyl ester;

3-[4-(2-(4-fluorophenyl)naphth-1-yloxy)phenyl]propanoic acid, butyl ester;

3-[4-(2-(4-methoxyphenyl)naphth-1-yloxy)phenyl]-propanoic acid, butyl ester;

3-[4-(2-(4-hydroxyphenyl)naphth-1-yloxy)phenyl]-propanoic acid, butyl ester;

3-[4-(2-(4-hydroxyphenyl)-6-hydroxynaphth-1-yloxy)phenyl]propanoic acid, hexyl ester;

3-[4-(2-(4-methoxyphenyl)-6-methoxynaphth-1-yloxy)phenyl]propanoic acid, hexyl ester;

4-[4-(2-(3-hydroxyphenyl)-6-hydroxynaphth-1-yloxy)phenyl]butanoic acid, ethyl ester;

4-[4-(2-($^4$-hydroxyphenyl)-$^6$-hydroxynaphth-1-yloxy)phenyl]butanoic acid, ethyl ester;

4-[4-(2-($^4$-methoxyphenyl)-$^6$-hydroxynaphth-1-yloxy)phenyl]butanoic acid, ethyl ester;

4-[4-(2-($^4$-methoxyphenyl)-6-methoxynaphth-1-yloxy)phenyl]butanoic acid, ethyl ester;

4-[4-(2-($^4$-hydroxyphenyl)-$^6$-hydroxynaphth-1-yloxy)phenyl]butanoic acid, ethyl ester;

4-[4-(2-($^4$-methoxyphenyl)-$^6$-methoxynaphth-1-yloxy)phenyl]butanoic acid, ethyl ester;

4-[4-(2-($^4$-hydroxyphenyl)-$^6$-hydroxynaphth-1-yloxy)phenyl]butanoic acid, pentyl ester;

4-[4-(2-($^4$-methoxyphenyl)-$^6$-methoxynaphth-1-yloxy)phenyl]butanoic acid, pentyl ester;

4-[4-(2-($^4$-hydroxyphenyl)-6-hydroxynaphth-1-yloxy)phenyl]butanoic acid, cyclohexyl ester;

4-[4-(2-($^4$-methoxyphenyl)-6-methoxynaphth-1-yloxy)phenyl]butanoic acid, cyclohexyl ester;

4-[4-(2-($^4$-hydroxyphenyl)-$^6$-hydroxynaphth-1-yloxy)phenyl]butanoic acid, phenyl ester;

4-[4-(2-($^4$-methoxyphenyl)-$^6$-methoxynaphth-1-yloxy)phenyl]butanoic acid, phenyl ester;

4-[4-(2-($^4$-hydroxyphenyl)-6-hydroxynaphth-1-yloxy)phenyl]butanoic acid, $^4$-methylphenyl ester; and 4-[4-(2-($^4$-methoxyphenyl)-$^6$-methoxynaphth-1-yloxy)phenyl]butanoic acid, $^4$-methylphenyl ester.

7. A compound according to claim 3 wherein $R^4$ is selected from the group consisting of $^1$-piperidinyl, 1-pyrrolidinyl, methyl-1-pyrrolidinyl, dimethyl-1-pyrrolidino, 4-morpholino, dimethylamino, diethylamino, diisopropylamino, and 1-hexamethyleneimino.

8. A compound as defined by claim 7 selected from the group consisting of

3-[4-(2-(4-hydroxyphenyl)naphth-1-yloxy)phenyl]-propenoic acid, N,N-diethylamide;

3-[4-(2-(4-methoxyphenyl)naphth-1-yloxy)phenyl]-propenoic acid, N,N-diethylamide;

3-[4-(2-(4-hydroxyphenyl)-6-hydroxynaphth-1-yloxy)phenyl]propenoic acid, N,N-dimethylamide;

3-[4-(2-(4-methoxyphenyl)-6-methoxynaphth-1-yloxy)phenyl]propenoic acid, N,N-dimethylamide;

3-[4-(2-(4-hydroxyphenyl)-6-hydroxynaphth-1-yloxy)phenyl]propenoic acid, 1-pyrrolidinylamide;

3-[4-(2-(4-methoxyphenyl)-6-methoxynaphth-1-yloxy)phenyl]propenoic acid, 1-pyrrolidinylamide;

3-[4-(2-phenyl-6-hydroxynaphth-1-yloxy)phenyl] propenoic acid, 1-piperidinylamide;

3-[4-(2-phenyl-6-methoxynaphth-1-yloxy)phenyl] propenoic acid, 1-piperidinylamide;

3-[4-(2-(4-hydroxyphenyl)naphth-1-yloxy)phenyl]-propenoic acid, 1-piperidinylamide;

3-[4-(2-(4-methoxyphenyl)naphth-1-yloxy)phenyl]-propenoic acid, 1-piperidinylamide;

3-[4-(2-(3-hydroxyphenyl)-6-hydroxynaphth-1-yloxy)phenyl]propenoic acid, 1-piperidinylamide;

3-[4-(2-(3-methoxyphenyl)-6-methoxynaphth-1-yloxy)phenyl]propenoic acid, 1-piperidinylamide;

3-[4-(2-(4-hydroxyphenyl)-6-hydroxynaphth-1-yloxy)phenyl]propenoic acid, 1-piperidinylamide;

3-[4-(2-(4-methoxyphenyl)-6-methoxynaphth-1-yloxy)phenyl]propenoic acid, 1-piperidinylamide;

4-[4-(2-(3-hydroxyphenyl)-6-hydroxynaphth-1-yloxy)phenyl]but-3-enoic acid, 1-piperidinylamide;

4-[4-(2-(3-methoxyphenyl)-6-methoxynaphth-1-yloxy) phenyl]but-3-enoic acid, 1-piperidinylamide;

4-[4-(2-(4-hydroxyphenyl)-6-hydroxynaphth-1-yloxy) phenyl]but-3-enoic acid, 1-piperidinylamide;

4-[4-(2-(4-methoxyphenyl)-6-methoxynaphth-1-yloxy) phenyl]but-3-enoic acid, 1-piperidinylamide;

4-[4-(2-(4-hydroxyphenyl)naphth-1-yloxy)phenyl]but-3-enoic acid, 1-piperidinylamide;

4-[4-(2-(4-methoxyphenyl)naphth-1-yloxy)phenyl]but-3-enoic acid, 1-piperidinylamide;

4-[4-(2-phenyl-6-hydroxynaphth-1-yloxy)phenyl]but-3-enoic acid, 1-piperidinylamide;

4-[4-(2-phenyl-6-methoxynaphth-1-yloxy)phenyl]but-3-enoic acid, 1-piperidinylamide;

3-[4-(2-(4-hydroxyphenyl)naphth-1-yloxy)phenyl]-propanoic acid, N,N-diethylamide;

3-[4-(2-(4-methoxyphenyl)naphth-1-yloxy)phenyl]-propanoic acid, N,N-diethylamide;

3-[4-(2-(3-hydroxyphenyl)-6-methoxynaphth-1-yloxy) phenyl]propanoic acid, 1-piperidinylamide;

3-[4-(2-(3-methoxyphenyl)-6-methoxynaphth-1-yloxy) phenyl]propanoic acid, 1-piperidinylamide;

3-[4-(2-(4-hydroxyphenyl)-6-methoxynaphth-1-yloxy) phenyl]propanoic acid, 1-piperidinylamide; and 3-[4-(2-(4-methoxyphenyl)-6-methoxynaphth-1-yloxy) phenyl]propanoic acid, 1-piperidinylamide.

9. A compound according to claim 2 selected from the group consisting of

1-[4-[3-(piperidin-1-yl)propyl]phenoxy]-2-(4-methoxyphenyl)-6-methoxynaphthalene;

1-[4-[3-(1-piperidinyl)propyl]phenoxy]-2-(3-methoxyphenyl)-6-methoxynaphthalene;

1-[4-[3-(1-piperidinyl)propyl]phenoxy]-2-(3,4-dimethoxyphenyl)-6-methoxynaphthalene;

1-[4-[3-(1-piperidinyl)propyl]phenoxy]-2-(3-fluorophenyl)-6-methoxynaphthalene;

1-[4-[3-(1-piperidinyl)propyl]phenoxy]-2-(4-chlorophenyl)-6-methoxynaphthalene;

1-[4-[3-(1-piperidinyl)propyl]phenoxy]-2-(4-methoxyphenyl)naphthalene;

1-[4-[3-(1-pyrolidinyl)propyl]phenoxy]-2-(4-methoxyphenyl)-6-methoxynaphthalene;

1-[4-[3-(N,N-dimethyl)propyl]phenoxy]-2-(4-methoxyphenyl)-6-methoxynaphthalene;

1-[4-[3-(1-hexamethyleneimino)propyl]phenoxy]-2-(4-methoxyphenyl)-6-methoxynaphthalene;

1-[4-[3-(N,N-dimethyl)propyl]phenoxy]-2-(4-methoxyphenyl)-6-methoxynaphthalene;

1-[4-[3-(1-pyrolidinyl)propyl]phenoxy]-2-(3-methoxyphenyl)-6-methoxynaphthalene;

1-[4-[3-(1-piperidinyl)prop-2-enyl]phenoxy]-2-(4-methoxyphenyl)-6-methoxynaphthalene;

1-[4-[3-(1-piperidinyl)prop-2-enyl]phenoxy]-2-(3-methoxyphenyl)-6-methoxynaphthalene;

1-[4-[3-(1-piperidinyl)prop-2-enyl]phenoxy]-2-(4-methoxyphenyl)naphthalene;

1-[4-[3-(1-piperidinyl)prop-2-enyl]phenoxy]-2-phenyl-6-methoxynaphthalene;

1-[4-[3-(1-hexamethyleneimino)prop-2-enyl]phenoxy]-2-(4-methoxyphenyl)-6-methoxynaphthalene;

1-[4-[3-(1-piperidinyl)prop-2-enyl]phenoxy]-2-(4-chlorophenyl)-6-methoxynaphthalene;

1-[4-[3-(N,N-dimethyl)prop-2-enyl]phenoxy]-2-(4-methoxyphenyl)-6-methoxynaphthalene;

1-[4-[4-(1-piperidinyl)but-3-enyl]phenoxy]-2-(4-methoxyphenyl)-6-methoxynaphthalene;

1-[4-[4-(1-piperidinyl)but-3-enyl]phenoxy]-2-(3-methoxyphenyl)-6-methoxynaphthalene;

1-[4-[4-(1-pyrolidinyl)but-3-enyl]phenoxy]-2-(4-methoxyphenyl)-6-methoxynaphthalene;

1-[4-[4-(1-piperidinyl)but-3-enyl]phenoxy]-2-(4-methoxyphenyl)naphthalene;

1-[4-[4-(1-piperidinyl)but-3-enyl]phenoxy]-2-phenyl-6-methoxynaphthalene;

1-[4-[4-(1-piperidinyl)but-3-enyl]phenoxy]-2-(3-fluorophenyl)-6-methoxynaphthalene;

1-[4-[4-(1-piperidinyl)butyl]phenoxy]-2-(4-methoxyphenyl)-6-methoxynaphthalene;

1-[4-[4-(1-piperidinyl)butyl]phenoxy]-2-(3-methoxyphenyl)-6-methoxynaphthalene;

1-[4-[4-(1-piperidinyl)butyl]phenoxy]-2-(4-methoxyphenyl)naphthalene;

1-[4-[4-(1-piperidinyl)butyl]phenoxy]-2-phenyl-6-methoxy-naphthalene;

1-[4-[4-(1-pyrolidinyl)butyl]phenoxy]-2-(4-methoxyphenyl)-6-methoxynaphthalene; and 1-[4-[4-(1-piperidinyl)butyl]phenoxy]-2-(4-fluorophenyl)-6-methoxynaphthalene.

10. A pharmaceutical formulation comprising an effective amount of a compound as defined by claim 1 in combination with a pharmaceutically acceptable carrier.

11. A pharmaceutical formulation according to claim 10 further comprising an effective amount of a compound selected from the group consisting of estrogen and progestin.

12. A method of inhibiting bone loss or bone resorption comprising administering to a patient in need of such treatment a compound of claim 1.

13. A method according to claim 12 wherein said bone loss or bone resorption is due to menopause or ovariectomy.

14. A method of lowering serum cholesterol levels comprising administering to a patient in need of such treatment an effective amount of a compound of claim 1.

* * * * *